(12) United States Patent
Wei

(10) Patent No.: US 9,642,868 B2
(45) Date of Patent: *May 9, 2017

(54) TOPICAL AGENTS FOR THE TREATMENT OF SENSORY DISCOMFORT IN THE NASAL CAVITY

(71) Applicant: Edward T. Wei, Berkeley, CA (US)

(72) Inventor: Edward T. Wei, Berkeley, CA (US)

( * ) Notice: Subject to any disclaimer, the term of this patent is extended or adjusted under 35 U.S.C. 154(b) by 59 days.

This patent is subject to a terminal disclaimer.

(21) Appl. No.: 14/545,014

(22) Filed: Mar. 16, 2015

(65) Prior Publication Data

US 2015/0265752 A1    Sep. 24, 2015

Related U.S. Application Data

(63) Continuation-in-part of application No. PCT/GB2013/052750, filed on Oct. 22, 2013, and a continuation-in-part of application No. PCT/GB2013/052751, filed on Oct. 22, 2013.

(30) Foreign Application Priority Data

Oct. 22, 2013  (WO) ................ PCT/GB2013/052750
Oct. 22, 2013  (WO) ................ PCT/GB2013/052751

(51) Int. Cl.
| | | |
|---|---|---|
| *A61K 31/66* | (2006.01) | |
| *A61M 35/00* | (2006.01) | |
| *A61K 9/00* | (2006.01) | |
| *A61F 13/40* | (2006.01) | |

(52) U.S. Cl.
CPC ............ *A61K 31/66* (2013.01); *A61K 9/0043* (2013.01); *A61M 35/006* (2013.01); *A61M 2210/0618* (2013.01)

(58) Field of Classification Search
CPC ................ A61K 31/66; A61K 9/0043; A61M 2210/0618; A61M 35/006
See application file for complete search history.

(56) References Cited

U.S. PATENT DOCUMENTS

| | | | | |
|---|---|---|---|---|
| 4,070,496 A | * | 1/1978 | Rowsell | ............... A23L 1/22614 131/276 |
| 6,410,046 B1 | * | 6/2002 | Lerner | ................. A61K 9/0009 424/400 |
| 8,133,502 B2 | * | 3/2012 | Clarot | ................. A61K 9/0043 424/400 |

* cited by examiner

*Primary Examiner* — Rachel Bredefeld

(57) ABSTRACT

The present discovery pertains generally to the field of therapeutic compounds. More specifically the present discovery pertains to certain di-alkyl-phosphinoyl-alkanes as described herein, DIPA-1-8 and DIPA-1-9, and 2-6 and 2-7 that are collectively referred to herein as "DAPA compounds", that are useful in the treatment of disorders (e.g., diseases) including: sensory discomfort (e.g., caused by inflammation, irritation, itch, or pain) in the nasal cavity. The applicant has found that localized delivery of DAPA compounds with a swab to the Kiesselbach's area of the human nose will relieve the discomforts of rhinitis and other nasal cavity discomforts.

3 Claims, 9 Drawing Sheets

FIGURE 1
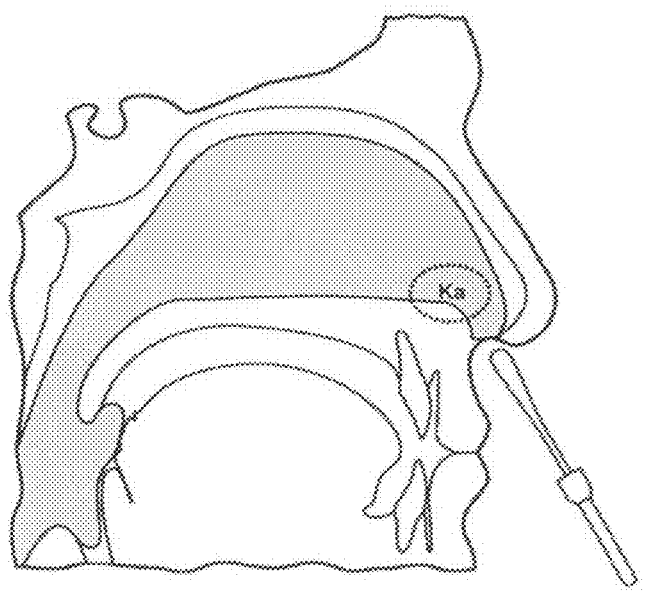
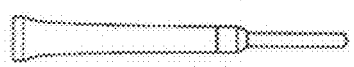
FIG.1 A
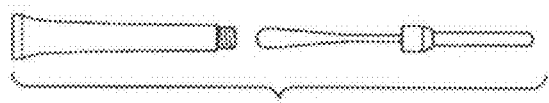
FIG.1 B

TOPICAL AGENTS FOR THE TREATMENT OF SENSORY DISCOMFORT IN THE NASAL CAVITY

CROSS-REFERENCE TO RELATED APPLICATIONS

This application is a continuation-in-part of International (PCT) Patent Application No PCT/GB2013/052750, filed Oct. 22, 2013 and International (PCT) Patent Application No PCT/GB2013/052751, filed Oct. 22, 2013, U.S. Ser. No. 14/544,355 filed Dec. 29, 2014.

Inventor: Edward Tak Wei

BACKGROUND OF THE INVENTION

Field of the Invention

The present invention pertains generally to the field of therapeutic compounds. More specifically the present invention pertains to certain 1-[Diisopropyl-phosphinoyl]-alkanes as described herein (DIPA-1-7, DIPA-1-8, and DIPA-1-9,) and certain 1-[Di-sec-butyl-phosphinoyl]-alkanes (2-6 and 2-7) that are useful in the treatment of disorders (e.g., diseases) and sensory discomfort (e.g., caused by inflammation, irritation, itch, or pain) originating from the nasal cavity. The present invention also pertains to pharmaceutical compositions comprising such compounds, and the use of swabs for topical delivery of such compounds and compositions to the nasal membranes, in particular to the region of the nasal membranes known as Kiesselbach's area.

Description of Related Art

Chemical sensory/cooling agents are molecules that can mimic the sensations of heat abstraction without a change in tissue temperatures. The exact sensations produced by chemicals depend on the selection of the active ingredient and the site and method of delivery. The term "chemical cooling agent" can be ambiguous because, for example, chemicals such as ethyl chloride as a gas, ethanol as a liquid, liquid nitrogen, or carbon dioxide as a solid, applied to the skin can evoke heat abstraction sensations by reducing tissue temperatures. In this application, chemical cooling agents will refer only to agents that elicit sensations of heat abstraction without a lowering of tissue temperatures.

Nasal stuffiness and congestion, and a sense of loss of patency and obstructed airflow, have many causes, the most common being "rhinitis", a technical term meaning the condition of inflammation of the membranes lining the nose. Rhinitis is characterized by nasal congestion, rhinorrhea ("runny nose"), sneezing, itching of the nose and/or post-nasal drainage. A common form of rhinitis is seasonal allergic rhinitis which is caused by seasonal aeroallergens such as pollens and molds [Seidman, M. D. et al. Clinical Practice Guideline: Allergic Rhinitis. Otolaryngol. Head Neck Surg. 152, S1-S43 (2015)]. Perennial allergic rhinitis is caused by perennial environmental aeroallergens such as dust mites, molds, animal allergens, or occupational allergens. Rhinitis can also be caused by food allergies. Some individuals, without evidence of allergic sensitization, will have rhinitis in reaction to nonspecific irritant stimuli such as cold dry air, perfumes, paint fumes, and cigarette smoke. This condition is called vasomotor rhinitis. Severe rhinitis may result from injury to the nasal membranes such as occurs after smoke inhalation, sinusitis, or after nasal surgery.

Rhinitis is also caused by the common cold virus. Initially, viral rhinitis is characterized by clear, watery rhinorrhea that is accompanied by sneezing and nasal obstruction. Edema of the nasal mucosa produces occlusion of the sinus ostia, with resulting facial pain, or of the Eustachian tube, with resulting ear fullness. Responsible viruses include rhinoviruses, respiratory syncytial virus, parainfluenza, influenza and adenoviruses. Fever may accompany viral rhinitis, especially if there is bacterial superinfection by streptococcal organisms.

The sinuses drain into the nasal cavity. Rhinosinusitis is inflammation of the mucosa of the nasal sinuses together with the nasal membranes. This condition is a major cause of breathing discomfort because it is accompanied by prolonged mucopurulent nasal discharge, facial pain and pressure, olfactory disturbance, and post-nasal drainage with cough.

Rhinitis is a common symptom. The prevalence of allergic rhinitis is estimated to be up to 20% of the general population. Individuals in the USA are estimated to have one or two bouts of the common cold per year. The economic burdens of rhinitis associated with allocation of health resources, from loss of work days, and from absence at schools are significant [Stewart, M. et al. Epidemiology and burden of nasal congestion. Int. J. Gen. Med. 3, 37-45 (2010)].

Pharmacological management of allergic rhinitis is a well-developed science. Effective medications for allergic rhinitis are the intra-nasally administered glucocorticosteroids [INS], intranasal antihistamines, and orally administered antihistamines. Sprays are used for topical treatments of the nasal membranes to deliver the active ingredients using manual pump-operated metered atomizers (e.g. Flonase®, Rhinocort®, Nasonex® and Nasocort®). The INS and antihistamines reduce nasal membrane inflammation and the symptoms and signs of allergic rhinitis. These compounds, in their current formulations have some side-effects such as nosebleeds [epistaxis], headaches, and pharyngitis for INS and bitter tastes for the intranasal antihistamines. Intranasal steroids are not effective for relieving the discomforts of infectious [e.g. viral] rhinitis, and have more limited efficacy for rhinosinusitis. INS and antihistamines are not less used for rhinitis caused by air pollutants wherein irritants directly damage the nasal mucosa.

Menthol, camphor and eucalyptus oil have been used since ancient times as remedies for nasal irritation and for refreshment of nasal sensations. These compounds may briefly provide cooling sensations in the nasal passages but are not effective for rhinitis. In fact these substances exacerbate nasal congestion and obstruction, especially in the late and delayed stages of rhinitis. In the laboratory, menthol is an irritant when instilled into the nasal passages of humans [Alenmyr, L. et al. TRPV1 and TRPA1 stimulation induces MUC5B secretion in the human nasal airway in vivo. Clin. Physiol. Funct. Imaging 31, 435-444 (2011)]. Menthol vapor delivered onto the membranes of the nasopharynx via orthograde or retrograde airflow [in the form of a menthol lozenge] has pungency and a cooling effect which briefly relieves nasal congestion. The pungency of menthol may stimulate vasoconstriction of the nasal blood vessels and this contributes to a brief decongestant action.

Other medications for nasal discomfort and rhinitis include sympathomimetic vasoconstrictors (decongestants) that reduce nasal blood flow and symptoms of congestion, but these compounds have a number of adverse side-effects, including rebound hyperemia (rhinitis medicamentosum). Zinc salts may shorten the duration of the common cold and thus reduce symptoms, but lozenges and syrups may have bad tastes and cause nausea [Singh, M. Zinc for the common cold (Review) Cochrane Library Database. (2014)]. There is a need for better medications to treat the signs and symptoms of nasal congestion and rhinitis.

It is a common experience that breathing cool air, for example at the seaside, will enhance the sense of fresh airflow in the nose. This effect has been demonstrated in the laboratory where subjects report a greater sense of nasal patency with lower nasal septum temperatures [Willatt et al. The role of the temperature of the nasal lining in the sensation of nasal patency. Clin. Otolaryngol. Allied Sci. 21, 519-523 (1996)]. Recently, it has been shown that peak mucosal heat loss in a critical region of the nose is a key correlate of the sense of nasal patency [Zhao, K. et al. Regional peak mucosal cooling predicts the perception of nasal patency. Laryngoscope 124, 589-595 (2014)]. This is a "Eureka!" event to me because it suggested that a strategy to mimic heat abstraction sensations in a localized anterior region of the nasal mucosa with a chemical agent may lead to a new method to treat the discomforts of nasal congestion.

Wei [AG-3-5: a chemical producing sensations of cold. J. Pharm. Pharmacol. 35: 110-112 (1983)]] discovered the cooling properties of icilin and gave this molecule its name. Wei [U.S. Pat. No. 6,933,301. Aug. 23, 2005] proposed that icilin administered into the nasal cavity may be useful for the relief of the symptoms of rhinitis, but this idea was not commercialized because of technical difficulties in formulating icilin for delivery into the nasal cavity.

Clarot and Hensley [U.S. Pat. No. 8,133,502] described the use of an applicator, enclosed in a sealed plastic container, for the delivery of a gelled composition to the nasal membranes. The active ingredient is selected from a group of moisturizer, a decongestant, or a homeopathic agent. Such enclosed swabs for nasal applications are now commercially available from Zicam [Nasal Swabs for Allergy Relief] and the listed active ingredients are Galphimia glauca, Histaminium hydrochloricum, Luffa operculata, and Sulfur. The label "Nasal Swabs with Cooling Menthol" is on the box of Zicam's swabs, but menthol is not listed under "Drug Facts" nor is the menthol content revealed.

BRIEF SUMMARY OF THE INVENTION

In one embodiment of the present invention, a composition is provided that comprises a 1-[Dialkyl-phosphinoyl]-alkane compound of Formula 1:

(O=)PR$_1$R$_2$R$_3$ wherein each of R$_1$, R$_2$, is either isopropyl or sec-butyl and R$_3$ is a linear alkyl group of 6 to 9 carbons.

Compounds of Formula 1 are formulated in an aqueous solution. The composition is usefully delivered in a therapeutically effective amount as a solution onto the membranes of the nasal cavity, preferably by means of a swab. The compound of Formula 1 is preferably represented by 1-[Diisopropyl-phosphinoyl]-octane [DIPA-1-8] or by 1-[Diisopropyl-phosphinoyl]-nonane [DIPA-1-9].

The preferred embodiments, DIPA-1-8 and DIPA-1-9 were selected because they do not cool or impart the sense of cold to the nostril skin nor do they exert a pungent sensation on the nasal mucosa. A cold sensation on the nostril skin is deemed unpleasant and will stimulate rhinorrhea. A pungent sensation, although capable of temporarily clearing the nasal passages by reflex vasoconstriction, is too short-lasting to be of therapeutic benefit. Instead, DIPA-1-8 and DIPA-1-9 were selected because they impart a mild, refreshing sensation to the nasal mucosa, without an effect on the nostril skin or pungency, and at therapeutic concentrations elicit a long-lasting enhancement of nasal patency and of reduced rhinorrhea.

In another aspect of the present invention, an device useful to relieve nasal cavity discomfort is provided that comprises a swab having one end carrying an absorbent material, the absorbent material having absorbed thereon an aqueous solution in which a 1-[Dialkyl-phosphinoyl]-alkane containing 14 or 15 carbons is present in the solution at a concentration of 1 to 10 mg/mL, wherein the rod is of sufficient construction to topically deliver a therapeutic amount of the 1-[Dialkyl-phosphinoyl]-alkane to the Kiesselbach's area of a human nose.

Thus, the swab can be saturated with the aqueous solution of Formula 1, and the swab is adapted to deliver or dispense, by wiping, at least one unit dose of a therapeutically effective composition to the nasal cavity surfaces. The composition to be delivered or dispensed preferably includes a compound of Formula 1, e.g DIPA1-8 or DIPA1-9. The active ingredient of Formula 1 is preferably in an amount of at least about 1 to 5 mg per mL of aqueous solution. By aqueous solution is meant a liquid that is at least 95% by weight of water.

In yet another aspect of the invention, a therapeutic article, useful for relieving nasal cavity discomfort, comprises a plurality of discrete doses of a molecule of Formula 1. A particularly preferred embodiment for practicing this, and all aspects of this, invention is DIPA1-8 or DIPA1-9.

An important aspect of this discovery was the identification of the preferred anatomical site within the nasal cavity for drug delivery. This site is the nasal mucosa located on the anterior inferior part of the septum, known as Kiesselbach's area or Little's area. Four nasal arteries confluently join [anastomose] at this location to form Kiesselbach's area [or plexus]. Identification of this small target area permits focused topical delivery of microgram doses to achieve therapeutic effect, thus avoiding more cumbersome and less efficient aerosolized spray or nose drops as methods of delivery.

Practice of this invention provides improved therapeutic benefit for the treatment of nasal cavity discomforts, such as the sensations of nasal obstruction and nasal congestion caused, for example, by allergic rhinitis, by rhinitis caused by irritants in the nasal cavity such as smoke, odors, and pollutants, by rhinitis caused by secretions associated with infections of the nose and throat, by symptoms of the "empty nose syndrome', and by rhinitis caused by rhinosinusitis. A particularly preferred method of treating nasal stuffiness in a human comprises intra-nasally administering, by wiping with a swab a liquid solution of a composition comprising a compound of Formula 1 onto Kiesselbach's area. Preferably, the compounds are in an aqueous solution of 1 to 5 mg/mL and delivered at a volume of 0.01 to 0.1 mL per nostril.

Surprisingly, in addition to improving the subjective feeling of nasal patency, some of the secondary objective signs of rhinitis, namely, sneezing and rhinorrhea were significantly attenuated by the preferred embodiments of this discovery. Furthermore, the treatment effects were long-lasting, being effective from 12 hr to days. The further advantages and aspects of the present invention will be understood by reading the following detailed description and the accompanying claims.

BRIEF DESCRIPTION OF THE SEVERAL VIEWS OF THE DRAWINGS

FIG. 1. is an illustration of the method of drug delivery to the Kiesselbach's area of the human nose. A swab previously encased in a plastic reservoir is removed from the casing and reservoir and inserted into the nasal vestibule. The solution comes into contact with Kiesselbach's area, marked as Ka in the circle.

DETAILED DESCRIPTION OF THE INVENTION

Figure 2:
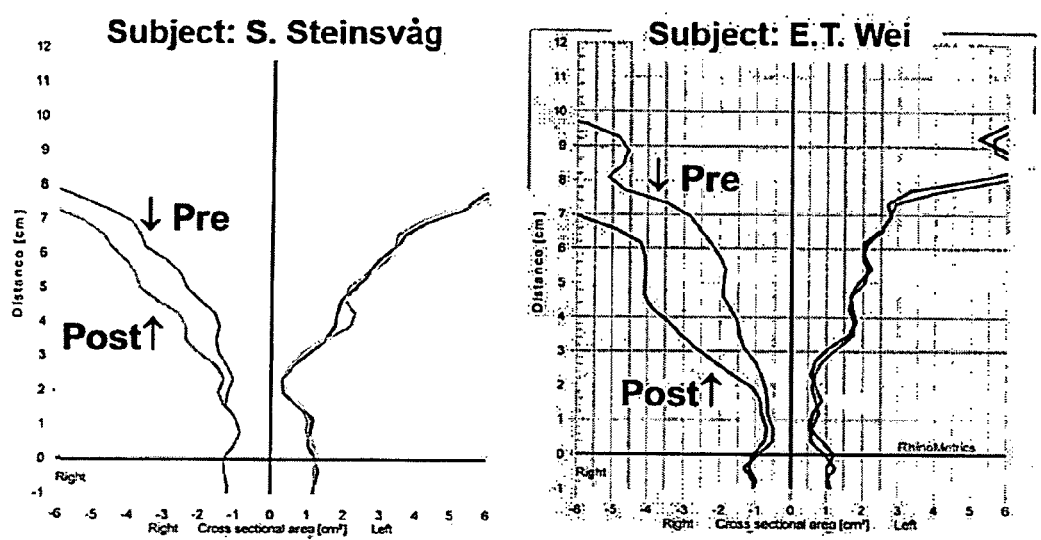
FIG. 2. shows the acoustic rhinometry graph tracing of two subjects before and after inhalation of ~5 mg of icilin powder. placed on the radial fossa. Readings were taken before and 15 to 30 min after inhalation. The units on the ordinates and abscissa of the graphs are in cm, and represent the dimensions of nasal cavity determined by the acoustic rhinometry instrument. For the Steinsvåg subject nasal cavity volume was increased by 37% and for the Wei subject by 53% after icilin inhalation.

The nares, the pair of openings below the tip of the nose, are the entrances to the respiratory tract. The nasal passages serve as a conduit for inspired and expired air. When these passages are congested or obstructed, the condition is perceived as uncomfortable. The nasal cavity bony surfaces, including the sinuses, are lined by tissue called mucosa. This mucosa contains blood vessels, nerves, and small glands that secrete mucus and fluids into the nasal cavity. The nasal mucosa is richly supplied by sensory nerves that detect pain, temperature, pressure and odor, and by motor nerves that regulate secretions and blood flow. The nasal mucosa humidifies and warms the inspired air, hence it receives a large blood flow and the cells maintain a high degree of metabolic activity. Inflammation of the nasal mucosa caused by allergy, infections, injury, or irritants and the like, will stimulate the mucosa to secrete fluids, to swell, and to obstruct. When the nasal membranes increase in volume, the area available through which air can pass is diminished, and therefore one experiences a sense of "stuffiness", resistance to inspiration, and a feeling of nasal obstruction and loss of patency. The nose can also become itchy and "runny" (rhinorrhea) and, as the fluids and discharges accumulate, the result is a feeling of congestion and discomfort.

The following descriptions give an over-view of some quantitative dimensions of nasal function. The normal air intake is about 10,000 liters per day and nasal secretions contribute about 30 ml of fluids to humidify each 1000 liters [300 mL per day is about the volume of a can of soda]. The relative humidity of dry air inhaled via the nose is about 60% when it goes past the nose, but it is only about 5% when the air is breathed through the mouth. The relative humidity of air in the bronchi is 100% at body temperature and this humidification, contributed by blood flow through the mucosa, is required to maintain ciliary activity and prevent epithelial changes in the bronchial mucosa. Desiccation of the bronchial surface for more than 2 to 3 hours can cause mucosal changes that result in thickening of secretions, irritation, and increased susceptibility to infection.

ABBREVIATIONS AND TERMINOLOGY

DAPA and DIPA compounds, DAPA and DIPA is the abbreviations for 1-[Dialkyl-phosphinoyl]-alkane and 1-[Diisopropyl-phosphinoyl]-alkane, respectively. 1-[Di-sec-butyl-phosphinoyl]-alkanes are also described in this application. The third alkyl group in the molecule may be described by a number: hence, 4, 5, 6, 7, 8, 9, and 10 correspond to the butyl, pentyl, hexyl, heptyl, octyl, nonyl, and decanyl side chain, respectively. These alkanes are linear or "normal [n]" in configuration, with the phosphinoyl group attached to the primary, or "1-" position, of the carbon chain in the third sidechain. The syntheses of DIPA-5 to 7 and DIPA-9 to 10 were not previously reported but Siddall et al. [Simplified preparation of some trisubstituted phosphine oxides. J. Chemical Engineering Data 10: 303-305, 1965] reported the synthesis of DIPA 1-8 in 1965. The biological activities of the DIPA compounds applied to any organismic surfaces [e.g Kiesselbach's area] have not been reported prior to this discovery.

Kiesselbach's area—Four of the five nasal arteries supplying the nasal mucosa anastomose to form a plexus on the anterior inferior part of the septum, known as Kiesselbach's area [or triangle, or plexus] or Little's area [see FIG. 1]. This area in the adult is about 0.5 inches long. Most nosebleeds [epistaxis] originate from this site because of the high blood flow, dense vascularity, and proximity of the vessels to the nasal luminal surface. Kiesselbach's area is about 0.6 to 0.8 cm behind the opening of the nostrils and is covered by respiratory epithelium which is non-keratinizing and a single cell layer [pseudostratified epithelium]. The tip of the nose and the epithelia of the nasal vestibule are like regular skin and have a keratinizing layer [stratum corneum] on top of multiple layers of cells [stratified epithelium]. The nerve endings infiltrate the basal region of the cells at its points of attachment to the basal membrane.

Nasal patency—is the subjective sensation of openness and smooth airflow in the nasal passages when breathing. Loss of patency may be reported as "nasal stuffiness" or "nasal blockage" and causes discomfort, and the subject may use mouth breathing which is undesirable because it desiccates the airway surfaces. Nasal congestion implies excess fluids in the nasal passages. The term "nasal obstruction" is used more often when there is a physical, for example anatomical or structural, hindrance to airflow. Rhinitis, the inflammation of the membranes in the nasal cavity, is most often associated with nasal congestion and nasal obstruction. In the "empty nose syndrome" there are severe breathing discomforts, including loss of the sense of patency, but the symptoms can occur without rhinitis or physical evidence of change in airflow or gas exchange [Sozansky, J. Pathophysiology of empty nose syndrome. Laryngoscope 125, 70-74 (2015)].

Swab—is defined by the Medical Dictionary as a wad of cotton or other absorbent material attached to the end of a rod, wire, or stick, used for applying medication, removing material, collecting bacteriological material, etc. The swab used in the studies here were Puritan® [Guildford, Me., USA] large cotton tipped applicators [REF 803-PCL] attached to a 3-inch plastic rod. The rod may be made of plastic (e.g. polystyrene) or wood, and the adsorbent material is preferably cotton or rayon with a predetermined mass (e.g. 40 to 100 mg of cotton). This apparatus is illustrated in FIG. 1. The absorbent material carries the active ingredient which is in a liquid solution. One end of the rod serves as a handle to manipulate the absorbent material to a correct position for application while the other end carries the absorbent material. The absorbent material is preferably saturated because it is bathed in the liquid solution. The amount of fluid off-loaded is determined by the mass of the absorbent material and the method of topical wiping. By experiment, it was found that a cotton or rayon mass of 40 to 100 mg per tip was optimal for a delivered volume of 20 to 50 μL per nostril. Further details are available in the section on "Delivery Unit."

Nasal Physiology and Pathophysiology

Nasal cavity volume is not fixed by anatomy but fluctuates with the amount of blood in the venous capacitance vessels of the nose. In the nasal cycle, the side of the nose that is increased in volume is filled with the blood that is used to heat the incoming air. The blood supply to the nasal mucosa comes from five arteries. Both the internal and external carotid circulations contribute to the arterial supply of the nasal cavity. The anterior and posterior ethmoid arteries, branches of the ophthalmic artery, enter the nose after passing through the orbit and the lamina papyracea. The sphenopalatine artery, a terminal branch of the external carotid artery, enters the nose through the posterior lateral inferior wall. Additional blood supply comes from the greater palantine artery and the superior labial artery. Four of these vessels [the posterior ethmoid artery does not participate] anastomose and form a plexus of fenestrated capillaries some of which face the respiratory surface and are the major source of fluids and heat for humidifying and warming the air in the nasal cavity. Intranasal trigeminal fibers are distributed throughout the nasal cavity and are described as intraepithelial free nerve endings arising from Aδ and C fibers of the nasopalatine and ethmoid branches of the trigeminal nerve. This neural network controls blood flow and secretions [Sahin-Yimaz A et al. Anatomy and physiology of the upper airway. Proc. Am. Thoracic Soc. 8:31-39, 2011].

It has been known for some time that an individual's perception of nasal patency [for example, on a visual analog scale of 0 to 10 with 0 for being clear and 10 for being blocked] is not readily correlated to objective measurements of nasal airflow or nasal cavity volume [see Zhao et al., 2014, vide supra]. Thus, physicians have been puzzled by the lack of consistent correlation between a patient's subjective complaints of congestion/blockage versus objective measurements, such as rhinomanometry for nasal airflow resistance, acoustic rhinometry for nasal cavity volume, and endoscopic examination of the nasal cavity. Without objective measurements of nasal function that relate to symptoms, medical treatment must rely the patient's opinions of patency for treatment success and this can lead to confusing outcomes.

Recent elegant studies by Zhao et al. [2014] may have solved this puzzle. Using a sophisticated "real-time" computational fluid dynamics (CFD) nasal airway model, Zhao et al. [2014] found that, in normal volunteers, the patency ratings was only correlated to CFD-simulated peak heat loss in the nasal mucosa at a location immediately posterior to the nasal vestibule, at a position called the anterior inferior septum. The sense of patency was associated the rate of heat abstraction from this localized region of the nasal mucosa.

The anterior inferior septum is also the location of Kiesellbach's area [Ka] or Little's area, named after the late $19^{th}$ anatomists who described it. Four nasal arteries anastomose at this location and form a plexus of about half an inch long. The location of Ka is shown in FIG. 1. Zhao et al. [2014] does not identify his "site" as being Kiesselbach's area but he noted that his active "site" is also a border where the keratinized nasal vestibular epithelium transitions to a non-keratinizing respiratory epithelium. Transitional epithelia in the body are generally densely innervated with sensory nerve endings [e.g. the margins of the eyelids, the inner border of the lips, and the margins of the anogenitalia].

Breathing cool air increases the sense of nasal patency. This is a fact of common experience, for example, breathing at the seaside. It has been shown in the laboratory when the inspired air temperature measured at the septum is kept at 25 to 35° C. there is a greater sense of patency at the lower temperature [Willatt et al., vide supra]. However, it is also well-known that cold and frigid air will evoke a "runny nose" or rhinorrhea, an event mediated by cholinergic nerves on serous glands of the nasal epithelium [Ostberg et al. Cold air induced rhinorrhea and high-dose ipratropium Arch. Otolaryngol. Head and Neck Surg. 113, 160-162 (1996)]. This condition has also been called a "skier's nose" and is quite common. Thus, cooling of the nasal cavity may increase secretions and exacerbate congestion. The negative effect of cooling on congestion is further shown by the fact that lowering the body temperature by immersion in cold water will cause vasodilation and increased nasal mucosal blood flow and hot water causes the nasal arteries to constrict [Lundqvist et al. Nasal reaction to changes in whole body temperature. Acta Otolaryngol. 113, 783-786 (1993)]. Thus, one cannot predict, ipso facto, that colder air temperatures will relieve congestion because cold causes rhinorrhea and increased nasal cavity volume.

The nasal afferents for detection of temperature are located in branches of the trigeminal nerve. The most likely receptor on the nerve endings mediating detection of coolness is the voltage-dependent cation channel called TRPM8, although a Grueneberg neuron receptor called CNGA3 may also participate [Mamasuew et al. The cyclic nucleotide-gated ion channel CNGA3 contributes to coolness-induced responses of Grueneberg ganglion neurons. *Cell. Mol. Life Sci.* 67, 1859-1869 (2010)]. Keh et al. [The menthol and cold sensation receptor TRPM8 in normal human nasal mucosa and rhinitis. Rhinology 49, 453-7 (2011)] have detected TRPM8 immunoreactivity in human nasal mucosa, closely associated with nerve fibers and blood vessels. The immunoreactive TRPM8 proteins in the nasal mucosa were not increased in patients with rhinitis. Keh et al. [2011] suggested that TRPM8 antagonists might have value in rhinitis. I propose here an opposite view; namely, TRPM8 agonists have beneficial effects in the nasal discomfort caused by rhinitis. In science there is often times confusion when one group says that the agonist will work, and another group advocates the antagonist. The data in this application clearly favor the agonists and not the antagonists.

The nerves and blood vessels of the nasal mucosa regulate the temperature and the humidification of air. The nerve endings participate in the inflammatory response by releasing transmitters, such as histamine, acetylcholine, CGRP, and substance P, that, together with cells of the immune system, control blood flow secretions. The sensors and effectors are highly concentrated in Kiesselbach's area, at the anatomical juncture for the detection of the air temperature entering the nostrils. At first, one might hypothesize that cooling agents administered intranasally will inhibit the sensations of congestion by masking the signals of fullness and distension that accompanies nasal congestion. But this view is not correct because inhalation of menthol or inhalation of very cold air have limited beneficial effects on nasal stuffiness in clinical situations and menthol and cold stimulate rhinorrhea. Decreasing body temperature increases nasal mucosal blood flow [presumably to warm the incoming air].

Hypothesis on Mechanism of Drug Action

Without being bound by theory, I propose here a mechanism of drug action that might explain the findings in this invention. To go over the main observations:

the delivery of microgram amounts of the DAPA compounds of this discovery to Kiesselbach's area inhibits all aspects of nasal dysfunction, including the subjective sensations of loss of patency, sneezing, itching, and rhinorrhea.

the benefit with one drug application for rhinitis is prolonged, for 12 hr and longer in some subjects there may be a disease-modifying effect of the drug so that conditions such as allergic rhinitis may be "cured" and there is no longer need for continued drug treatment the intensity of the sensations of cold on the nose is not correlated to the efficacy of drug action because analogs that produce intense cold, e.g. DIPA-1-7, are not as effective as compounds that produce mild cooling sensations in the nasal cavity, e.g. DIPA-1-9 the selection of the active ingredient is based on the avoidance of excess cold sensation on nostril skin, and an optimal mild cooling of the nasal mucosa: hence the choice of active ingredient is not based on receptor potency, but on selective activity on nasal mucosa the onset of drug action to relieve congestion and to reduce nasal secretions occurs quickly, within 5 to 10 min after application of the compound to Kiesselbach's area, and the subjective description of the drug effect is "Amazing!".

this type of drug action has not been previously described for the treatment of nasal discomfort and is qualitatively distinct from the actions of intranasal glucocorticosteroids or antihistamines But what is the physiological mechanism of drug action for such a profound pharmacological effect? It is important to remember that the nasal mucosa not only warms the air to body temperature but also humidifies the air to 100% relative humidity. Approximately 300 mL of water, about the volume of a can of soda, is added by the nose to the inhaled air each day. If the humidification process is reduced then the rhinitis is shut off. Kiesselbach's area, with its high density of blood vessels, capillary fenestrations, and nerve endings, is the ideal location for such integrative and regulatory functions. When small arteries constrict and post-capillary venules become less permeable, fluid leakage into the mucosa is inhibited. Kiesselbach's area is the body's sensor and air humidifier.

But what is the drug signal conveyed by the TRPM8 agonist? Earlier, I have noted that icilin ointment applied to the lips or to the perianal skin will convey the sense of "wetness", an effect that is distinct from cooling. More recently, I reported that CPS-030 [WS-30], a cooling agent, applied to the ocular margins also produced the distinct sensation of wetness [U.S. Ser. No. 13/261,061]. It is possible that there are "wetness" sensing mechanisms in the nasal mucosa, to detect osmolality and tonicity, so when the air is perceived as 100% saturated with water, the local reflexes of vasculature and serous glands no longer add or secrete fluids into the nasal cavity. The hypothesis is that the key drug action is to tell the sensors that the inhaled air is optimally at 100% saturation and the air temperature is optimal and will not cause excessive heat loss. The system is set at a "comfort zone" and the humidification system can go on "stand-by".

When viewed in this manner, it can be inferred that inflammation of the nasal mucosa disrupts the body's sensors and the engines for warming and humidifying, and that rhinorrhea, the excess secretion of fluids into the nasal cavity, is an attempt of the humidifier to respond to the disruption. Surprisingly, the results here suggest the DIPA drug signal is not just providing symptomatic relief, but the drug action is also modifying the course of the inflammation. The subjects describe the initial effect as "Amazing", but the rhinitis also disappears for a prolonged time!. A disease-modifying drug action is possible if the drug action reduces inflammation.

Inflammation is the reaction of tissues to local injury. The elements in Kiesselbach's area react to inflammation with subjective discomfort, and vascular and secretory responses. A drug agent that reduces "perception" of the inflammatory signal and "re-sets" the regulatory network to the correct parameters can attenuate the subsequent reaction of tissues and alter the course of the inflammatory response. This type of drug action may be thought of as potent inhibitor of "neurogenic inflammation", a concept that has been discussed by students of inflammation. This is the first time that this type of potent drug action on the nasal mucosa has been identified.

The rationale for selection of the active ingredient is also a key component of this discovery. For the first time, it is pointed out that stimulation of cold on the nostril's keratinized skin, including the epithelia of the vestibule, is undesirable because the cold sensations are unpleasant and stimualate rhinorrhea. Based on an analysis of the bioactivity of these analogs in the laboratory animal, a rationale was identified to select the agonists that will optimally stimulate the nasal mucosa, a non-keratinizing respiratory epithelium.

Nasal Congestion and Icilin

Earlier, Wei [1983] described the cooling properties of icilin and gave this molecule its name. Icilin is at least 10× more potent than l-menthol on the TRPM8 receptor, and it does not have a mint odor, irritancy, or pungency. Wei [U.S. Pat. No. 6,933,301. Aug. 23, 2005] reported that icilin, when given to individuals with allergic rhinitis, relieved the subjective feeling of nasal congestion.

These observations were made:
  inhaled icilin powder elicits cooling sensations of nasal membranes in normal individuals,
  in subject with allergic rhinitis there is relief from nasal congestion within 5 to 10 min after delivery of icilin into the nasal cavity,
  the cooling and relief of symptoms after icilin can last for at least six hours,
  the effective dose of icilin is 2 to 4 mg per nostril In this discovery further studies have been made to clarify the mechanisms of action of icilin, and to establish "proof-of-concept" data that TRPM8 agonists may be used to relieve nasal congestion.

It was found that:
  the effects of icilin in the nasal cavity are variable if icilin is delivered in its natural chemical state, namely, a fluffy yellow powder
  it is difficult, if not impossible, to reliably dissolve icilin in standard solvents for delivery into the nasal cavity in a formulation
  icilin is not stable when suspended in aqueous solution
  when icilin powder is formulated as 20% wt/wt in mannitol powder with a Speedmixer® [using the principle of dual asymmetric centrifugation] and delivered via nasal inhalation by placement of the mixture on the radial fossa, and then inhaled, consistent pharmacological effects of increased nasal airflow and patency are obtained
  inhalation of icilin does not cause nasal irritation or rhinorrhea
  in normal individuals, without airway obstruction or rhinitis, inhalation of icilin increases the nasal cavity volume by 37 to 53%, as measured by acoustic rhinometry
  icilin inhalation increases peak nasal inspiratory flow by about 29%
  on a visual analog scale, icilin increases nasal patency and nasal patency is noted as "cool and clear" in individuals with allergic rhinitis or with the common cold These results are further described in greater detail in this application.

Alternative TRPM8 Agonists for Nasal Delivery to Kiesselbach's Area.

The observations of icilin effects in the human nasal cavity were very encouraging, but the difficulty of formulating and delivering an icilin-type molecule agonist to the site described by Zhao et al. [2014] prompted the search for alternative TRPM8 agonists that might accomplish the same drug effect.

These criteria were defined as a desirable in a candidate active pharmacological ingredient [API]:
  the API should be easy to formulate, ideally, the active ingredient should be water soluble at an effective therapeutic concentration at standard temperature and pressure
  the API should be easily delivered to nasal mucosa in the midline, immediately posterior to the nasal vestibule, at the site called Kiesselbach's area
  the API should be selective for TRPM8 and not active at other TRP sensory channels such as TRPV1 and TRPA1
  the API when delivered should increase the sense of nasal patency to a degree of therapeutic relevance
  the API should not over stimulate cold-sensing elements to cause "stinging cold" or cold rhinorrhea
  the API should be chemically stable in solution and not have odor or irritancy, and have an adequate safety margin
  the API should be potent, for example, at 1 to 10 mg/mL, and have a duration of drug action that is clinically meaningful
  the API should penetrate tissue barriers to reach targets in the presence of exudates in the nasal cavity
  the API should act within 5 min after topical delivery, thus favoring patient compliance and cooperation As shown in the studies described below, "ideal" API candidates were identified and comprise molecules of Formula 1; in particular, the entities known as DIPA-1-8 and DIPA-1-9. Furthermore, a delivery system was devised to topically administer the API to Kiesselbach's area.

Study 1

Acoustic Rhinometry (AR) and Peak Nasal Inspiratory Flow (PNIF)

In acoustic rhinometry (AR) a sound pulse enters the nasal cavity, where it is reflected due to changes in the local impedances. From the incident and reflected sound signal, an algorithm is used to calculate an area-distance relationship. This method for measuring nasal cavity volume has been validated in humans and animals using other techniques (e.g. CT-scanning, MR scanning and fluid displacement) and is now a standard tool in the clinic. [Kjaergaard, T et al. Nasal congestion index: A measure for nasal obstruction. Laryngoscope 119, 1628-1632 (2009)].

AR and PNIF are often used in the evaluation of airflow in human subjects. AR measures nasal airway cross-sectional area as a function of longitudinal distance along the nasal passage way following the path of an acoustic pulse. This method utilizes automated instruments [Rhinometrics SRE2100, ver. 2.5, Lunge Denmark]. Trained operators record three curves from both nasal cavities, and these values are averaged for each side. Then test substances are put on the radial fossa and inhaled, and 15 to 30 min later, the AR measurement is repeated.

PNIF is a physiological measure indicating the peak nasal airflow achieved during inspiration. A portable peak flow meter (In-check DIAL: Alliance Tech Medical Inc., Granbury, Tex.) was used. Three trials were conducted to obtain satisfactory maximal inspirations with the patient in an upright position. Maximum flow registration is given in L/min.

Prof. Sverre Steinsvåg is an expert rhinologist with thoughtful publications on the subject of nasal patency and its measurements [Kjaergaard, T., Cvancarova, M. & Steinsvåg, S. K. Does nasal obstruction mean that the nose is obstructed? Laryngoscope 118, 1476-1481 (2008)]. Experiments were conducted in Steinsvåg's laboratory in Kristiansand, Norway, and the results shown in FIG. 2.

FIG. 2 shows the acoustic rhinometry graph tracing of two subjects before [Pre] and after [Post] inhalation of ~5 mg of icilin powder [20% by weight in mannitol] placed on the radial fossa. Readings were taken before and 15 to 30 min after inhalation. The units on the ordinates and abscissa of the graphs are in cm, and represent the dimensions of nasal cavity determined by the acoustic rhinometry instrument. For the first subject [Steinsvåg] nasal cavity volume was increased by 37% and for the second subject [Wei] by 53% after icilin inhalation.

Here is his description of the experiment: "I have now tested icilin on myself. The subjective experience of openness was immediate, prominent and still lasting after 2 hours. As the enclosed acoustic rhinometric measurement shows, icilin appears to have an obvious effect on the nasal cavity. The straightline in the middle represents the nasal septum. The lines on its left and right sides represent the lateral nasal walls. On the right side, you can see that the pre-measurement line is more medially placed than the corresponding post-measurement line. This movement of the lateral nasal wall laterally documents the decongestion. The minimal cross sectional area increases by 26% and the volumes increases by 37%. We do not see the same effect on the left side, probably due to the nasal cycle."

In a second subject (Wei), the results were even more dramatic (FIG. 2). The minimal cross sectional area increased by 45% and the volumes increased by 53%. PNIF increased from 53 to 65 L/min in one trial and from 55 to 75 L/min in a second trial, clearly indicating an improvement in airflow.

After icilin inhalation, peak nasal inspiratory flow was increased by 23% in one subject, and 32% in the second subject.

These big changes in nasal cavity volume and peak nasal inspiratory flow were unexpected and surprising because they occurred in normal healthy individuals without nasal obstruction. Nasal physiology is capable of these responses, for example, during exercise or to sympathomimetic decongestants, but this is the first time that a compound like icilin has been shown to produce these effects.

Study 2
Formulation Problems of Icilin for Delivery: Chemical Instability.

In the studies described above, and the results shown in FIG. 2, the icilin was inhaled as a 5 mg dose from the radial fossa [anatomical snuff box], i.e. from the back of the hand in the depression between the thumb and fore-finger. The icilin was formulated as 20% by weight in mannitol to give an estimated delivered dose of 5 mg of icilin, and the inhaled total dose of 25 mg.

Although efficacious, inhalation of a powder from the radial fossa is not an accepted method of drug delivery. The nostrils become white from the powder and the individual is suspected of illicit drug use. Attempts to formulate icilin for liquid delivery as a spray or nose drop, however, was not successful. Icilin is unstable in standard solvents such as water and propanediol [FIG. 3].

The assay method was based on high performance liquid chromatography (HPLC) with spectrophotometry detection. The chromatograph was a Gold System model (Beckman, USA) with model 126 dual pump, model 166 and 168 ultraviolet spectrophotometry detectors, and the relevant data system with the Gold version 7.12 software. The chromatography separation column was: the Nucleosil reversed phase C-18, 5 µm sorbent; dimensions: 250×4.6 mm. The precolumn of the same sorbent was used and substituted by the new one at regular intervals. The analytical chemistry was conducted by Prof Sergey Burov of the Institute of Macromolecular Chemistry at St. Petersburg, Russia.

Figure 3:
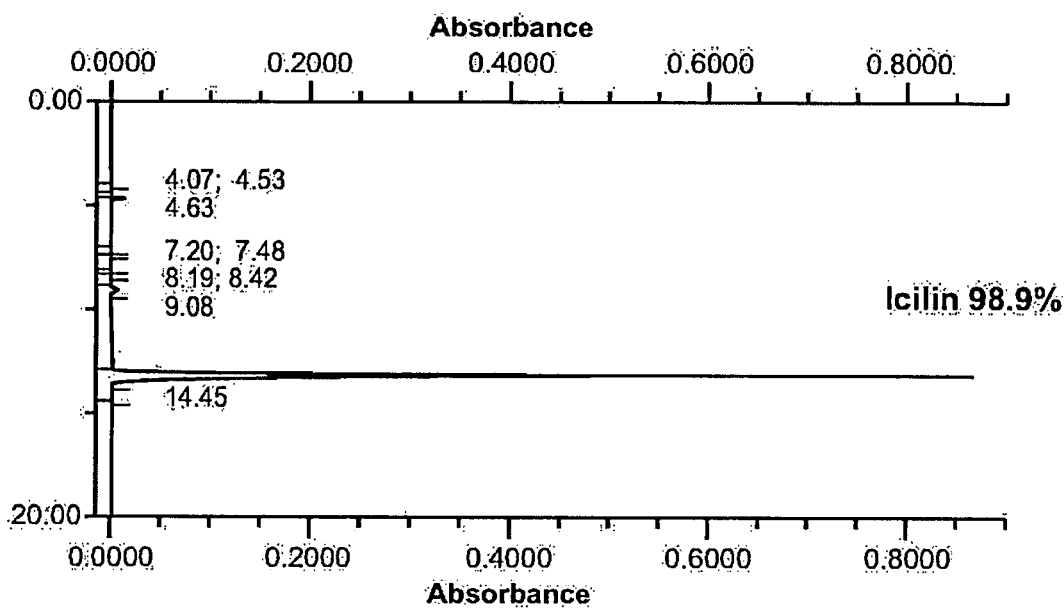
FIG. 3. is a graph of a high-pressure liquid chromatogram of icilin, freshly prepared (top panel) and after 3 weeks storage in distilled water (lower panel). The chromatogram shows that icilin is degraded from 98.9% purity to 68.5% purity after storage in water.
Figure 3:
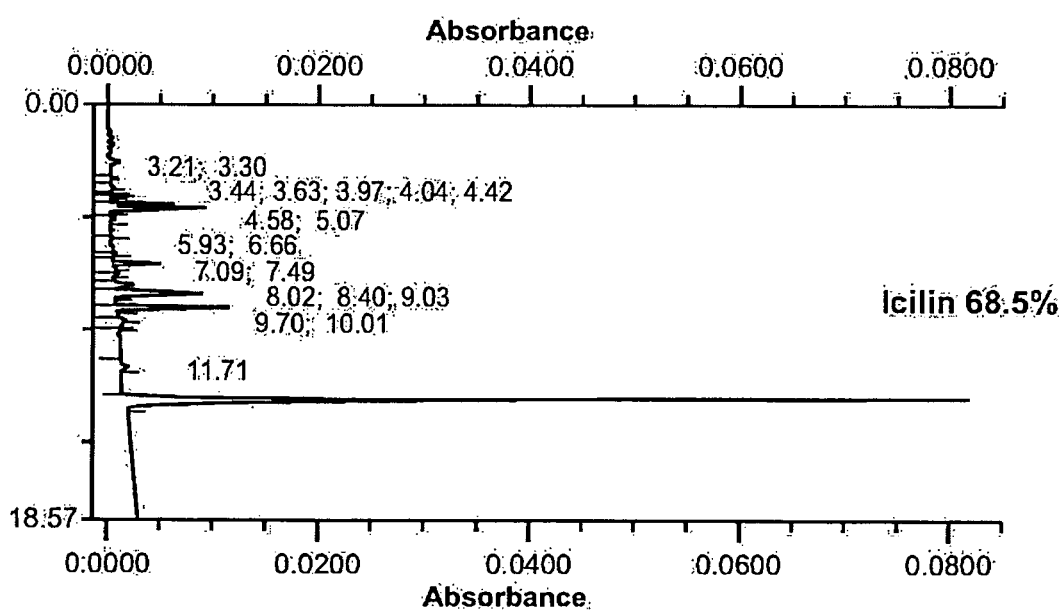

As shown in FIG. 3, icilin suspended for several weeks in distilled water breaks up. The sample degraded from 98.6% to 68.5% purity. After several years of research effort to formulate icilin into an acceptable liquid delivery system, the effort was abandoned. Delivery as a dry powder is still feasible, but resources required to develop, standardize, and deliver a dry powder formulation are substantial. It was more practical to find an alternative active pharmacological ingredient [API].

FIG. 3 is a graph of a high-pressure liquid chromatogram of icilin, freshly prepared [left panel] and after 3 weeks storage in distilled water [right panel]. The chromatogram shows that icilin is degraded from 98.9% purity to 68.5% purity after storage in water.

Study 3
1-[Dialkyl-phosphinoyl]-alkanes

Known Phosphine Oxides: The [Dialkyl-phosphinoyl]-alkanes [e.g. total number of carbons ≤16] are solvent-like molecules that require only several [1 to 3] steps for synthesis. They are also known as trialkylphosphine oxides, but the preferred term now is [Dialkyl-phosphinoyl]-alkane [DAPA]. If two of the alkyl groups are isopropyl, the DAPA is abbreviated to DIPA [Diisopropyl-phosphinoyl-alkane].

Rowsell and Spring [Phosphine oxides having a physiological cooling effect. U.S. Pat. No. 4,070,496. Jan. 24, 1978], described a range of phosphine oxides which have a physiological cooling effect on skin and on the mucous membranes of the body, particularly the mouth, throat and gastrointestinal tract [columns 3 and 4 therein]. Ten (10) of the compounds shown therein (Table 1) have one isopropyl group (shown as iso-$C_3H_7$). None of the compounds synthesized by Rowsell and Spring has two isopropyl groups [Table 1]. Rowsell and Spring considered the use of the trialkylphopshine oxides as a decongestant in combination with the sympathomimetic α-adrenergic receptor agonist ephedrine, but is silent on the use of such compounds as a single medicinal agent for the treatment of nasal inflammation.

Siddall et al. [Simplified preparation of some trisubstituted phosphine oxides. J. Chemical Engineering Data 10: 303-305, 1965] reported the synthesis of 1-[Diisopropyl-phosphinoyl]-octane [DIPA-1-8]. No reports on any bioactivity of this or other diisopropyl-phosphinoyl-alkane compounds have previously been made.

TABLE 1

Compounds in Rowsell et al., 1978: P(=O)$R_1R_2R_3$

| # | $R_1$ | $R_2$ | $R_3$ |
|---|---|---|---|
| 2 | iso-$C_3H_7$ | sec-$C_4H_9$ | n-$C_7H_{15}$ |
| 3 | iso-$C_3H_7$ | sec-$C_4H_9$ | n-$C_8H_{17}$ |
| 7 | iso-$C_3H_7$ | sec-$C_4H_9$ | n-$C_6H_{13}$ |
| 8 | iso-$C_3H_7$ | cyclo-$C_5H_9$ | n-$C_6H_{13}$ |
| 11 | iso-$C_3H_7$ | cyclo-$C_5H_9$ | n-$C_7H_{15}$ |
| 12 | iso-$C_3H_7$ | iso-$C_5H_{11}$ | n-$C_6H_{13}$ |
| 15 | iso-$C_3H_7$ | iso-$C_5H_{11}$ | n-$C_7H_{15}$ |
| 26 | iso-$C_3H_7$ | n-$C_6H_{13}$ | n-$C_6H_{13}$ |
| 30 | iso-$C_3H_7$ | cyclo-$C_5H_9$ | n-$C_8H_{17}$ |
| 47 | n-$C_4H_9$ | (n-$C_4H_9$)($C_2H_5$)$CHCH_2$ | iso-$C_3H_7$ |

In this discovery, DAPA compounds were synthesized and tested on:

receptor activation assays in vivo animal assays human subjects with nasal discomfort.

From these studies four candidate API were identified that may have utility in the relief of nasal discomfort from irritants, allergens, and inflammation.

Chemical Synthesis

The DIPA compounds were prepared by the following general method: 100 mL (23.7 g, ~200 mmol) of isopropylmagnesium chloride (or sec-butylmagnesium chloride in the case of the di-sec-butyl derivatives) were obtained from Acros, as a 25% solution in tetrahydrofuran (THF) and placed under nitrogen in a 500 mL flask (with a stir bar). Diethylphosphite solution in THF (from Aldrich, D99234; 8.25 g, 60.6 mmol in 50 mL) was added drop-wise. After approximately 30 minutes, the reaction mixture warmed up to boiling. The reaction mixture was stirred for an extra 30 min, followed by a drop-wise addition of the appropriate n-alkyl iodide solution in THF (from TCI; 60 mmol in 20 mL). The reactive mixture was then stirred overnight at room temperature. The reaction mixture was diluted with water, transferred to a separatory funnel, acidified with acetic acid (~10 mL), and extracted twice with ether. The ether layer was washed with water and evaporated (RotaVap Buchi, bath temperature 40° C.). The light brown oil was distilled under high vacuum [0.5 mm Hg]. The final products, verified by mass as determined by mass spectrometry, were transparent liquids that were colourless or slightly pale yellow and had boiling points in the range of 120 to 130° C.

Several samples of DIPA-1-7 or DIPA-1-8 were sent for detailed analysis by GC-MS (NCE Corporation, Pleasanton, Calif., USA, www.nceanalytical.com). Analysis was conducted on an Agilent GC/MS system 6890/5973 equipped with a TraceGold TG-624 column, with helium as the carrier gas [flow rate: 1.6 mL/min] and the injector port set at 220° C. [split ratio 50:1, temperature program: 100 to 240° C.]. The TIC [total ion chromatogram] showed the main components as having a retention time of 18 to 19 min, with the detected peaks accounting for 97.2% of the total area. Similar results of 97 to 99% purity were obtained with other samples. When gas chromatography [equipped with a flame ionization detector (Dong Wha Corporation, Seoul, Korea)] was used as the analytical system, synthesized compounds were also found to be 97 to 99% chromatographically pure.

The following compounds were prepared by this method where Table 2A and Table 2B compounds are embodiments of the invention.

TABLE 2A

Chemical structures of diisopropyl-analogs.

| Code | Chemical Name | Chemical Structure |
|---|---|---|
| DIPA-1-5 | 1-[Diisopropyl-phosphinoyl]-pentane | 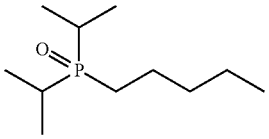 |
| DIPA-1-6 | 1-[Diisopropyl-phosphinoyl]-hexane | 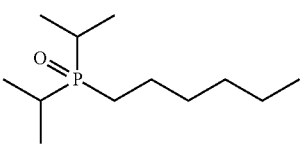 |
| DIPA-1-7 | 1-[Diisopropyl-phosphinoyl]-heptane | 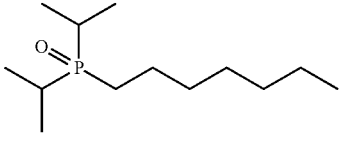 |
| DIPA-1-8 | 1-[Diisopropyl-phosphinoyl]-octane | 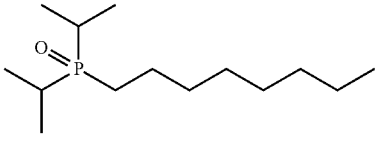 [SMILES: CCCCCCCCP(=O)(C(C)C)C(C)C] |
| DIPA-1-9 | 1-[Diisopropyl-phosphinoyl]-nonane | 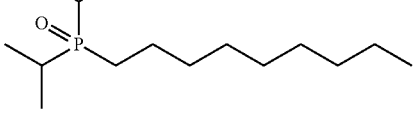 |

TABLE 2B

Chemical structures of di-sec-butyl-analogs.

| Code | Chemical Name | Chemical Structure |
|---|---|---|
| 2-4 | 1-[Di-sec-butyl-phosphinoyl]-butane | 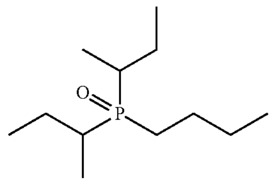 |
| 2-5 | 1-[Di-sec-butyl-phosphinoyl]-pentane | 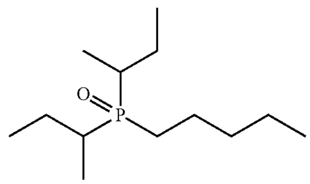 |
| 2-6 | 1-[Di-sec-butyl-phosphinoyl]-hexane | 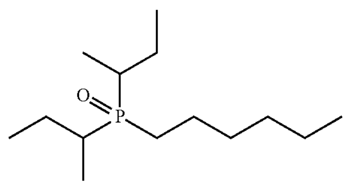 [SMILES: CCCCCCP(=O)(C(C)CC)C(C)CC] |
| 2-7 | 1-[Di-sec-butyl-phosphinoyl]-heptane | 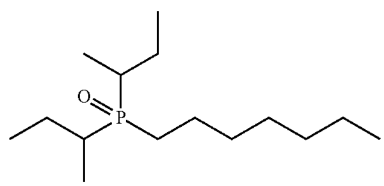 [SMILES: CCCCCCCP(=O)(C(C)CC)C(C)CC] |
| 2-8 | 1-[Di-sec-butyl-phosphinoyl]-octane | 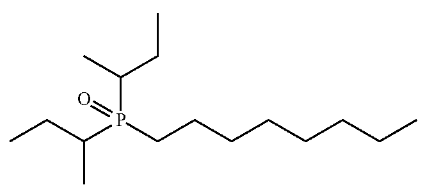 [SMILES: CCCCCCCCP(=O)(C(C)CC)C(C)CC] |
| 3-1 | 1-[Diisobutyl-phosphinoyl]-pentane | 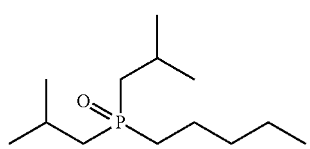 |
| 3-2 | 1-[Di-sec-butyl-phosphinoyl]-3-methyl-butane | 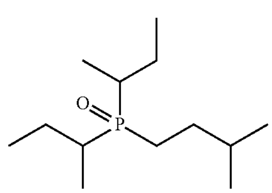 |

General Observations on DAPA Compounds

DAPA compounds are colorless liquids with a density less than water [0.7 to 0.8 g/cc]. They are generally soluble in water or saline at up to 20 mg/mL, or for the compounds with greater than or equal to 16 carbon atoms, a homogeneous emulsion of very fine droplets. When DAPA compounds are applied to the facial skin as an aqueous solution at 5 to 10 mg/mL there is no irritation or blanching. For certain analogs, contacting the facial skin with a solution at a concentration of 5-20 mg/mL produce a sensation of strong cooling within 1 min especially when applied to periorbital skin. The effects are strong on non-keratinzing tissues such as the lining of the upper digestive tract and the ocular margins. The effects of these compounds after intranasal instillation have not been reported in the literature.

The present applicant has found that the intranasal sensations obtained are very much influenced by the method of drug delivery. Thus, nose drops are not feasible for delivery for the simple reason that the drops rapidly go through the turbinates, down the nasopharynx, and into the oral cavity. The drug action is not localized. The same situation holds for an aqueous spray: the distribution and the perceived sensation is quite variable, and delivery of the active ingredient is perceived in the nasopharynx and oropharynx. The swab method is optimally adapted for localized drug delivery to Kiesselbach's area.

Perinasal administration of the DAPA compounds will leave a residue on the nostril skin. For the more potent compounds such as DIPA-1-7, 2-6, and 2-7 there is a prolonged cooling sensation on the nostril skin. For some subjects, this is perceived as uncomfortable and not desirable. DIPA-1-8 and DIPA-1-9 have minimal effects on skin sensations.

The pharmacological effects of DIPA-1-8 and DIPA-1-9 are clearly differentiated from the sympathomimetic decongestants. DIPA-1-9 does not cause blanching of the skin or reduce redness from the blood vessels of the eyelids which are classical signs of α-adrenergic sympathomimetic activity. These compounds have a mild cooling action on human nasal mucosa, an effect that is not seen with sympathomimetic decongestants. Sympathomimetic agonists such as clonidine do not interact do not activate TRPM8 [Bavencoffe, A. et al. The transient receptor potential channel TRPM8 is inhibited via the α2A adrenoreceptor signaling pathway. J. Biol. Chem. 285, 9410-9419 (2010)]. The long durations of action of DIPA-1-8 and DIPA-1-9 are also not seen with the standard sympathomimetic decongestants.

Note that the diisopropyl groups of the DIPA compounds of this invention do not have a chiral center but each of the sec-butyl groups in compounds of the Di-sec-butyl-phosphinoyl series has a chiral centre, and that each chiral centre may independently be in the (R) or (S) configuration. As a consequence, a compound such as 2-6 has four possible stereoisomers: two optically active stereoisomers (i.e., R,R and S,S), and two optically inactive meso forms (i.e., R,S and S,R). Unless otherwise indicated, a reference to Di-sec-butyl-phosphinoyl compounds is intended to be reference to any one of the four stereoisomers, and any mixture of any two or more of the four stereoisomers. The absence of stereoisomers in the DIPA compounds is an advantage in drug development over molecules containing sec-butyl groups because current regulations often require that each enantiomer be either synthesized or isolated separately and then individually evaluated for toxicological activities.

Figure 6:
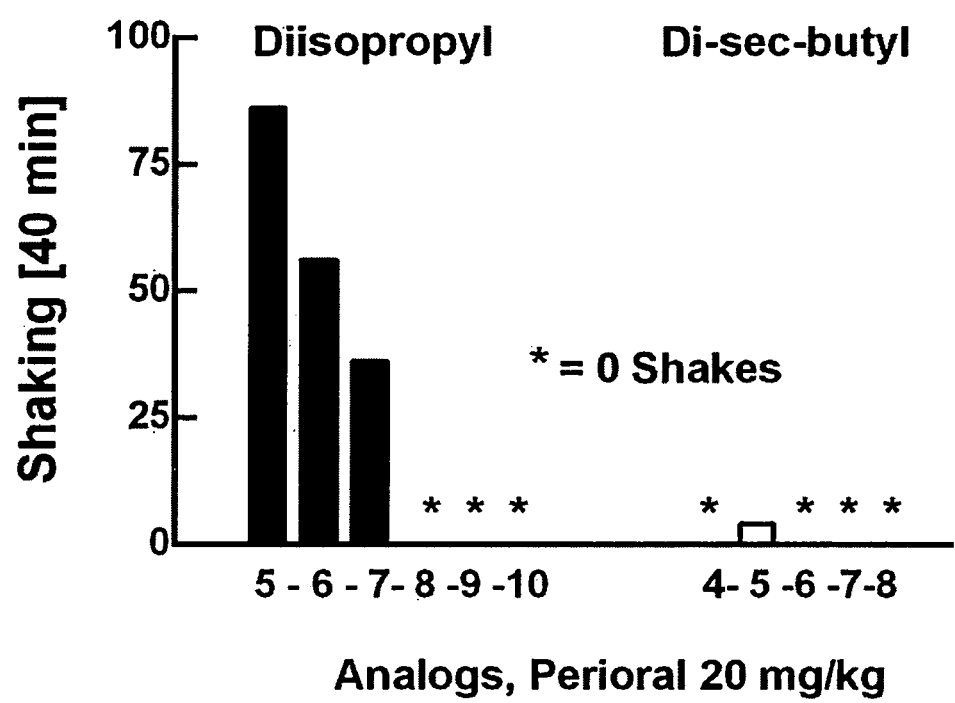
FIG. 6. is a graph showing shaking frequency of pentobarbital-anesthetized male rats after perioral administration of test compounds at 20 mg/kg with a gavage needle. Shaking frequency was counted for 40 min. The surprising lack of activity in the di-sec-butyl-phosphinoyl analogs is noted. The numbers on the abscissa represent the number of carbons in one of the n-alkyl side-chain: that is, the 4-5-6-7-8-9-10 represents the butyl, pentyl, hexyl, heptyl, octyl, nonyl and decanyl group, respectively.
Figure 7:
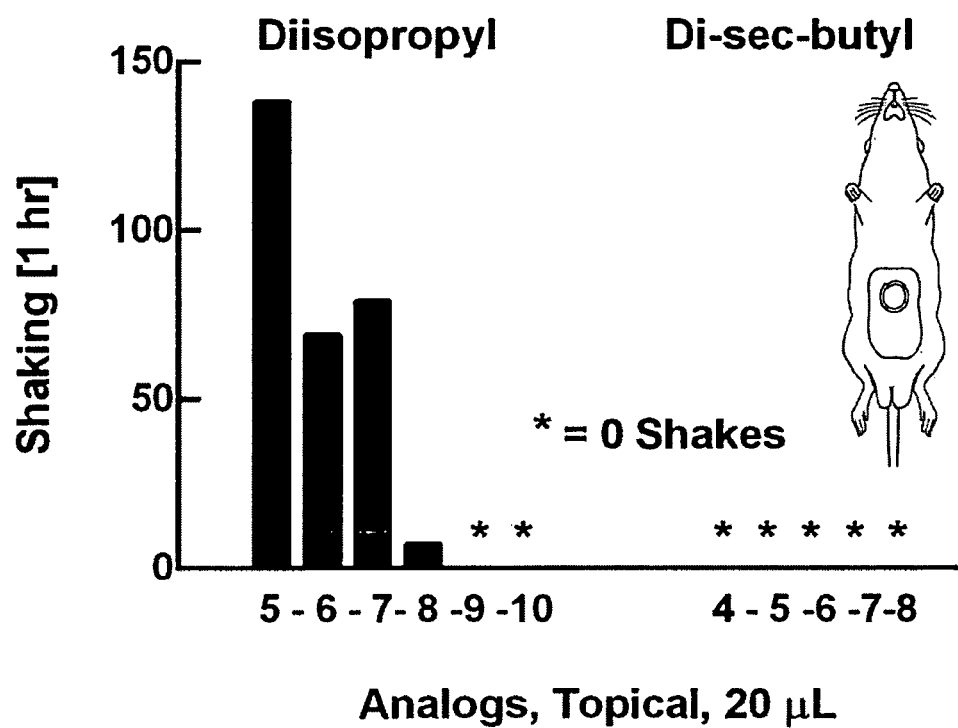
FIG. 7. is a graph showing shaking frequency of pentobarbital-anesthetized male rats after 20 μL of the pure test compounds was delivered onto the abdominal skin. Test substances were applied with a micropipette to the center of a circle enclosed by cream on the shaved skin, as shown in the cartoon insert on the graph. Shaking frequency was counted for 1 hr. The surprising lack of activity in the di-sec-butyl-phosphinoyl analogs after transdermal delivery is noted. The numbers on the abscissa represent the number of carbons in one of the n-alkyl side-chain: that is, the 4-5-6-7-8-9-10 represents the butyl, pentyl, hexyl, heptyl, octyl, nonyl and decanyl group, respectively.

The effects of diisopropyl versus the di-sec-butyl congeners were strikingly different in laboratory rats when given by the perioral or topical routes. [FIG. 6 and FIG. 7 and data in Table 4]. Perioral or topical application of DIPA analogs [DIPA-1-5, DIPA-1-6, DIPA-1-7] elicits vigorous shaking in the whole animal, but this effect is hardly seen with the di-sec-butyl congeners. This is because DIPA-1-5, DIPA-1-6, and DIPA-1-7 are able to penetrate the membrane barriers in the gut and keratinized skin. When given intravenously, the di-sec-butyl analogs are active [FIG. 8].

Terminology Used

Compositions: One aspect of the present discovery pertains to a composition (e.g., a pharmaceutical composition) comprising a DAPA compound, as described herein, and a pharmaceutically acceptable carrier, diluent, or excipient. Another aspect of the present discovery pertains to a method of preparing a composition (e.g., a pharmaceutical composition) comprising mixing a DAPA compound, as described herein, and a pharmaceutically acceptable aqueous solution. In one embodiment, the composition comprises the DAPA compound as an aqueous solution at a concentration of 0.5-20 mg/mL. The composition may be provided with suitable packaging and/or in a suitable container. For example, the composition may be provided as a swab or suitable tipped applicator carrying a DAPA compound or a composition comprising a DAPA compound.

Discomfort of the Nasal Cavity: In one embodiment (e.g., of use in methods of therapy, of use in the manufacture of medicaments, of methods of treatment), the treatment is treatment of sensory discomfort.

The term "sensory discomfort", as used herein, relates to irritation, itch, pain, or other dysesthesias (abnormal sensations; such as "stuffiness", congestion, obstruction, burning sensations, or feeling the presence of a foreign body, or pins and needles) from the nasal cavity surfaces. The term implies activation of nociceptors located on sensory nerve endings of the body. Nociceptors are stimulated, for example, by high or low temperatures, mechanical pressure, chemicals (e.g., capsaicin, acidity, pollutants, etc.), injury, inflammation, and inflammatory mediators. A compound, such as DIPA-1-8 or DIPA-1-9, that decreases sensory discomfort, can be termed an anti-nociceptive agent.

In one embodiment, the sensory discomfort is relieved by topical application of a medication onto the Kiesselbach's area using a swab saturated with an aqueous formulation of the active ingredient In one embodiment, the treatment is treatment of rhinitis and sinusitis. In one embodiment, the treatment is treatment of the symptoms of the "empty nose syndrome". In one embodiment, the treatment is treatment of nasal irritation from air pollutants. In one embodiment, the treatment is treatment of heat discomfort. In one embodiment, the treatment is treatment of heat stress. In one embodiment, the treatment is treatment of heat-related fatigue and to improve athletic performance. In one embodiment, the treatment is to refresh breathing sensations, to reduce snoring, and to reduce sleep apnea. In one embodiment, the treatment is treatment of flushing and/or night sweats (vasomotor symptoms) in a post-menopausal woman. In one embodiment, the treatment is treatment is to convey a sense of refreshment to breathing in a human.

Treatment: The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment." Treatment to enhance the basal levels of cognitive or physical performance of individuals who are considered normal or healthy is also included.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Routes of Administration: The term "topical application", as used herein, refers to delivery onto surfaces of the nasal cavity contact with air.

Subject/Patient may be a mammal, for example, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human. In one preferred embodiment, the subject/patient is a human.

Dosage: The dose and dosing regimen can be on an "as needed basis" or twice daily, depending on the severity of the condition being treated. Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

Delivery Systems and Tissue Targets

There are currently no topical antinociceptive (pain-suppressant) compounds that have strong efficacy on sensory discomfort from non-keratinizng stratified epithelium such as the respiratory epithelium of the nasal cavity. Ketorolac is approved for use, but it is not active for the nasal discomforts of congestion and obstruction. Treatment is focused on the inflammatory processes underlying the rhinitis as the best way to treat sensory discomfort from the nasal cavity.

FIG. 1 is an illustration of the method of drug delivery to the Kiesselbach's area of the human nose. A swab is previously encased in a plastic reservoir [1A] and saturated with an aqueous solution containing the active ingredient. The swab is removed from the casing and reservoir [1B] inserted into the nasal vestibule and the nostril lightly compressed so the solution optimally comes into contact with Kiesselbach's area, marked as Ka in the circle on the figure. Kiesselbach's area is the target for drug delivery. The choice of this target is discussed in final summary section of this application.

The delivery of the DIPA compounds can be achieved with the compound dissolved in purified water or isotonic saline or phosphate buffered saline. An example of the delivery device is shown in FIG. 1. For a liquid vehicle, a preferred concentration of the DIPA compound is in the range of 0.5 to 5 mg/mL. A preferred amount of the DIPA compound delivered at the site of application is 0.01 to 5 mg.

The pre-medicated swabs are usually packaged as a single-use sealed unit or in a multi-unit dispenser. For single units, suitable wrapper materials are those which are relatively vapor impermeable, to prevent drying out of the wipe, and able to form a removable seal. A "reservoir" contains the liquid formulation of the active ingredient (e.g. 0.5 to 1.0 mL) sufficient to saturate the absorbent material. The wrapping material of the "reservoir" is not permeable to liquids and may, for example, be cellophane or polystyrene, or other forms of plastic. The reservoir can also be a bottle of solution from which multiple doses may be acquired with individual disposable applicators. Examples of suitable absorbent materials for practicing this discovery include cotton, polyamide (20% Nylon)-polyester, and rayon (70%)-polyester (30%).

Examples of these swab applicators in individual units are known as SwabDose™ from Unicep Corporation (1702 Industrial Drive, Sandpoint, Id., USA), and the Pro-Swabs™ from American Empire Manufacturing (3828 Hawthorne Court, Waukegan, Ill., USA). Each applicator tip is saturated by dipping the absorbent material of the tip (e.g., 40 to 100 mg of cotton) in 0.5 to 1.5 mL of an aqueous solution of a DIPA compound and packaged in an individual container. A less expensive method is to wrap single units in moisture-proof cellophane with a peelable seal. Alternatively, a solution containing a DIPA compound may be supplied in a reservoir bottle with multiple individual applicators. For example, Puritan 803-PCL applicators are ideal cotton-tipped applicators attached to a 3-inch (~7.5 cm) polystyrene rod for delivery of a DIPA compound onto the periorbital skin.

A medicated swab for nasal membranes can be manufactured without a rigid container. For example, a sophisticated device is made by the S & B. Co., Ltd. Masan-Si, Korea [see www.snbglobal.com]. The apparatus, a "Magic Bar" maintains a solution above a cotton tip by capillary action. Twisting the hollow tube containing the solution allows the liquid to descend from the reservoir onto the cotton tip and be ready for delivery. The swab tip is not enclosed. This delivery device is less expensive to make per unit. Alternatively, the swab tip can be enclosed within a peelable, water-impermeable cellophane wrapping. This is also a less expensive method of making a single unit swab delivery system.

For application to the nasal cavity, the individual is instructed to gently insert the tip of the applicator cream into the opening of the nostrils [the nasal vestibule], and, after removal of the tip, to gently compress the nostrils with the thumb and forefinger towards the center of the nose. The instructions for application may include teaching the individual to repeat application, or "topping up", to ensure that sufficient composition is delivered to the target. Once the subject has learned what to expect, the individual can adjust the dosage (e.g., by dabbing more liquid at the medial site), as needed, to achieve the desired effect. It has been observed that individuals learn how to effectively apply the cooling agent after one or two trials and do so without difficulty.

Little is directly known about the neurophysiology of tissue targets in the nasal cavity [except for olfaction]. The surface is innervated by a branch of the trigeminal nerve. The terminology for describing the sensations of the nasal surfaces is not standardized. For example, menthol lozenges cool the nasopharynx, but it is not clear if it cools the turbinates. Inhaled menthol vapors are pungent and cause vasoconstriction, but it is not clear if these sensations can be described as cool or cold. Breathing frigid air causes sting and rhinorrhea. Only breathing cool air, for example, at the seaside convey the right degree of coolness and the sense of patency. This sensation is pleasurable, but the exact air temperature and humidity for capturing this sensation have not been defined.

There is a general view that "TRP-" ion channel receptors (A1, M8, and V1 to 4) are the principal physiological elements for physiological temperature detection. The TRPM8 receptor is the one that responds to sensory/cooling agents such as menthol and icilin [McKemy et al. Identification of a cold receptor reveals a general role for TRP channels in thermosensation, Nature, 416, 52-58, 2002]. TRPM8 is a protein with 1104-amino acid residues and has six transmembrane domains. Activation of this receptor by lowering ambient temperature results in opening of pores of transmembrane loop and non-specific cation entry into the cell. Depolarization of TRPM8 receptors on sensory neurons may then transmit signals primarily via Aδ (and some C) fibres.

While this concept for the role of TRPM8 in sensory physiology may be valid for detecting physical changes in temperature, the interpretation of the sensory effects of chemical agents such as menthol and icilin are more complex. Menthol not only stimulates TRPM8 in vitro, but also TRPV3, a receptor associated with warmth and glycinergic transmission [Macpherson et al. More than cool: promiscuous relationships of menthol and other sensory compounds. Mol Cell Neurosci 32:335-343, 2006: Sherkheli et al., Supercooling agent icilin blocks a warmth-sensing ion channel TRPV3, Scientific World Journal, 2012: 982725, 2012: Cho et al. TRPA1-like channels enhance glycinergic transmission in medullary dorsal horn neurons. J Neurochem 122:691-701, 2012]. Thus, menthol and icilin are called "promiscuous" agents and are not selective for one receptor protein.

The Applicant has screened a large database of cooling agents for sensory effects on the skin [keratinizing] and the ocular rim [non-keratinizing] and found that there are distinct responsive elements in the two types of epithelia [Wei. Sensory/cooling agents for skin discomfort. Journal Skin Barrier Research 14: 5-12, 2012].

The epithelia of the nares and the nasal vestibule is keratinizing, but then transitions to respiratory epithelium [non-keratinizing] in Kiesselbach's area. When one examines the structure-activity relationships (SAR) of the DIPA compounds [Formula 1] on keratinized skin, it is noted that when $R_1=R_2=$isopropyl and $R_3=$n-hexyl ($C_6$) or n-heptyl ($C_7$), then strong penetrating cooling is observed. Cooling of long duration is obtained on non-keratinizing epithelia with $R_3=$n-octyl ($C_8$) and n-nonyl ($C_9$). However, when $R_1=R_2=$sec-butyl dynamic cooling is observed when $R_3=$n-pentyl to n-heptyl ($C_5$ to $C_7$). As shown in the studies described herein, the distinction between diisopropyl and di-sec-butyl compounds is also seen in animal studies on shaking behavior.

Shaking behaviour is a rapid alternating contraction of the supination and pronation muscles about the spinal axis, and is readily observed and counted. Fur-coated and feathered animals—when wet and cold—shake, like a wet dog [Dickerson et al., Wet mammals shake at tuned frequencies to dry. J. Royal Society, Interface 9, 3208-3218, 2012; Ortega-Jimenez, V. M. et al. Aerial shaking performance of wet Anna's hummingbirds. J. Royal Society, Interface 9, 1093-9, 2012; Wei, Pharmacological aspects of shaking behavior produced by TRH, AG-3-5, and morphine withdrawal, Federation Proc. 40: 1491-1496, 1981].

"Wet-dog shaking" has been studied in detail in animals. Rats can shake their head, the upper torso, or the shaking can be sufficiently violent to affect the whole body and make the animal lose its balance. DIPA-1-7 and DIPA-1-8 elicit the vigorous type of shaking, but DIPA-1-9 does not. The purpose or survival value of shaking to fur-coated and feathered organisms is to remove water droplets trapped on or near the skin. Removal of the water droplets on or near the skin by shaking reduces the organism's need to expend energy to remove the water by evaporation. The likely equivalent behaviour to shaking in humans is shivering, a condition caused by generalized sensations of coolness/cold. Human subjects recovering from the deep hypothermia of anaesthesia manifest vigorous shaking; a condition called post-anaesthetic shivering.

For the DAPA compounds the shaking frequency seen after intravenous injection is a good approximation of the compound's potency for producing cold when administered into the nasal cavity surfaces.

Test compounds were also evaluated on receptor assays: on cloned hTRPM8 channel (encoded by the human TRPM8 gene, expressed in CHO cells) using a Fluo-8 calcium kit and a Fluorescence Imaging Plate Reader (FLIP-RTETRA™) instrument. The specificity of the test compounds were examined on TRPV1 channels (human TRPV1 gene expressed in HEK293 cells) and TRPA1 channels (human TRPA1 gene expressed in CHO cells). ChanTest Corporation, 14656 Neo Parkway, Cleveland, Ohio 44128, USA, was the contractor for these tests.

Selection of Active Ingredient

Ideally, an active pharmaceutical ingredient (API) formulated for delivery to the nasal epithelium should be chemically stable, non-toxic, and sufficiently long-acting and potent to activate the mechanisms that result in a sense of refreshed breathing and a reduction of nasal discomfort. The API should be dissolved and evenly dispersed in a composition so that during manufacture the formulation maintains a constant concentration. The final product should meet standards of cleanliness and sterility. For purposes of formulation, the API can be a liquid at standard conditions of temperature and pressure (STP) and that is evenly dissolved in aqueous solutions at neutral pH and/or isotonicity. Sterility of the final product can be optimally achieved by using purified reagents and filtration through micropore filters, heating, or irradiation. Standard excipients, such as preservatives, may be added to optimize the formulations, but the important ingredients should be preferably soluble in aqueous media such as purified water, isotonic saline, or phosphate buffers.

For a given individual, the perceived sensation is a function of the particular cooling agent, the dose, the vehicle used to carry the cooling agent, the method of topical delivery, and the nature of the target surfaces. The Applicant has screened a number of candidate compounds, including diverse compounds such as p-menthane carboxamides and icilin [Wei, 2012 vide supra]. The studies here identify DIPA-1-8, DIPA-1-9, 2-6 and 2-7 as having the preferred desired properties of an ideal API for the nasal cavity epithelium to refresh, to reduce rhinorrhea, and to exert an anti-nociceptive effect. These analogs are selected because they produce mild cooling on nasal mucosa and do not produce excessive cooling on nasal skin.

A key factor to the successful management of nasal discomfort is the water-solubility of the active ingredient for delivery to Kiesselbach's area. A water-soluble API has tremendous advantages for ease and for uniformity of delivery to the target. If a chemical is not soluble in water, solvents and excipients must be used. The solvent or matrix has to be free of unpleasant effects on the nasal mucosa. If the chemical can be administered as a semi-solid gel or powder, the particles size distribution of the active ingredient has to be controlled The applicant has screened a number of water soluble and water insoluble compounds and the results are described in Case Study 5. For water soluble compounds such as CPS-030 [WS-30] [U.S. Ser. No. 13/261,061], (L)-Monomenthane-3yl carbonate [RightCool™ monomenthyl glutarate], and 3-(1-Methoxyl)propane-1,2-diol [Cooler 10] were tested. The goal was to determine if such compounds can accelerate the sense of patency. It was found that CPS-030 at 5 mg/mL produced immediate sensations of coolness, but this was also felt on the skin of the nostrils, and there was a sense of wetness. Monomenthyl glutarate and Cooler 10, which are water soluble, were not active at 8 mg/mL Thus, CPS-030 could potentially be used as an enhancer of the DAPA compounds, to inform the patient that a drug had been delivered to the nose.

Water insoluble compounds may be useful for chronic rhinosinusitis or the "empty nose syndrome" because these disease conditions are long-lasting. With the correct formulations, e.g. milling and suspension into very fine particles or the incorporation of these compounds into gels, these water insoluble compounds, based on their chemical structure and reported pharmacological properties, are reasonable choices for prolonging duration of action if combined with DAPA compounds. These are some candidate compound: icilin; CPS-125 [2-isopropyl-5-methyl-cyclohexanecarboxylic acid [4-(pyrimidin-2-ylsulfamoyl)-phenyl]-amide]; CPS-195 [,2-Isopropyl-5-methyl-cyclohexanecarboxylic acid [2'-hydroxy-2'-(3"-hydroxy-phenyl)-ethyl]-N-methyl-amide]; Ax-8 [((1R,2S,5R)-2-isopropyl-5-methyl-cyclohexane-carbonyl)-amino]-acetic acid isopropyl ester; Ax-10 (R)-2-[((1R,2S,5R)-2-isopropyl-5-methyl-cyclohexanecarbonyl)-amino]-propionic acid isopropyl ester; (1R,2S,5R)-2-isopropyl-5-methyl-N-(2-(pyridin-2-yl)-ethyl-cyclohexanecarbox-amide; (1R,2S,5R)-N-(4-(cyanomethyl)-phenyl)-2-isopropyl-5-methylcyclohexyl carboxamide, and "M8-Ag" (4-[5-(4-chlorophenyl)-4-phenyl-4H-1,2,4-triazol-3-yl]morpholine [Patel, R. Anti-hyperalgesic effects of a novel TRPM8 agonist in neuropathic rats: A comparison with topical menthol. Pain 155, 2097-107 (2014)].

To summarize the design concepts that lead to the selection of the API, the delivery system, and the site of delivery, as being suitable for the practice of the discovery:

Icilin, a prototype non-irritating cooling agent, applied to the nasal membranes reduced nasal discomfort. A world-renowned rhinologist helped characterize the mechanisms of action of icilin on nasal cavity volume and nasal resistance. The laboratory results were clear and without ambiguity. Icilin, however, could not be developed as a single drug because of technical difficulties in formulation and instability of the icilin molecule in solution.

DAPA compounds were identified that were soluble in water at up to 20 mg/mL. These compounds are stable to heat, and exerted a potent therapeutic effect on nasal discomfort and inflammation at applied concentration of 1 to 10 mg/mL. In animal studies, tachyphylaxis does not develop to repeat applications.

The receptor target for DAPA compounds was ascertained in in vitro studies. The lead candidate was selective for TRPM8 and not for TRPV1 or TRPA1.

The biological activity of DAPA compounds was defined in an animal model of "wet-dog shakes". The perioral, topical/dermal, and intravenous activates were compared, and the selective differentiation of diisopropyl analogs from di-sec-butyl analogs was established.

The rationale for selecting Kiesselbach's area as a site for drug delivery was established. This observation reduces the need for drug delivery to other sites of the nasal surfaces, e.g. on the vestibular wall, on the mucosa of the turbinates, or on the nasopharynx.

The delivery system was developed using swabs, including packaging of the API into UniCep Swabdose® units for experiment.

In volunteers with rhinitis and nasal discomfort, the efficacy of four compounds for reducing nasal discomfort and rhinitis was established.

Compounds that produced strong cold on keratinized nasal skin, e.g. DIPA1-7, were considered less desirable than compounds that mildly refreshed the nasal mucosa [a non-keratinizing surface] of Kiesselbach's area. DIPA1-8 and DIPA1-9, were chosen as lead candidates.

Tests in human volunteers showed that four compounds, especially DIPA-1-8 and DIPA-1-9, were effective for relieving sensory discomfort from rhinitis and nasal pollutants. In normal subjects, there was enhanced refreshed breathing, and improved athletic performance. 2-6 applied intranasally was found to attenuate the discomfort of "night sweats".

Details for: Athletic Performance, Vasomotor Symptoms, Pharmaceutical Adjunct

The primary focus of this discovery is to treat and relieve the nasal stuffiness and discomfort associated with nasal congestion. Surprisingly, it was discovered that "rhinitis", a technical term describing inflammation of the nasal membranes was also ameliorated by the treatment. The sneezing, and itching of the nose was stopped by treatment. The swabs have other uses, as described below.

It is a natural desire of humans to want to perform better, either physically or mentally. Recently, there has been a surge of interest in the use of cryotherapy to improve athletic performance. Cryotherapy is defined as " . . . the lowering of tissue temperature (locally or generally) by the withdrawal of heat from the body to achieve a therapeutic objective . . . . " External pre-cooling by heat abstraction, for example, by immersion in ice or by wearing a vest packed with ice, can improve work endurance in a hot environment. An increase in physical work output of ~5% can be shown for tasks of approximately 30 min [Grahn D A et al. Heat extraction through the palm of one hand improves aerobic exercise endurance in a hot environment. J Appl Physiol 99:972-978, 2005]. Heat exhaustion limits work and this occurs when core body temperature approaches 40° C. (104° F.). Pre-cooling (or internal cooling, for example, by drinking an ice slurry) slows down the rate of heat accumulation.

As found in Case Study 3, delivery of DIPA-1-9 to a tennis player improved the sense of airflow and nasal patency and improved athletic performance. It is possible that a feeling of coolness in the nasal cavity and the body can improve athletic performance. Intranasal delivery of DIPA-1-8, DIPA1-9, 2-6 and 2-7 to Kiesselbach's area may be able to achieve this effect.

Flushing (vasodilation) and sweating occur on the body when the brain's thermoregulatory system perceives a need to lower body temperature. After menopause, at least one-third of women experience "hot flushes" or "night sweats" (i.e., brief but repetitive episodes of feeling warm and flushed, and daytime and nighttime sweating). Replacement estrogens may alleviate symptoms but there are uncertainties if hormone replacement therapy (HRT) is safe. Sweating episodes that occur at night and in the early morning hours are inconvenient because the bed-sheets become wet and it is burdensome to change the bed-sheets on a daily or frequent basis. Episodes of "hot flushes/night sweats" can occur as frequently as 14 episodes per week. Aside from HRT, current alternative methods of therapy, such as yoga, acupuncture, and phytoestrogens, have limited if any effectiveness.

The DAPA compounds of this discovery are potent agents that can enter the bloodstream and exert systemic effects after delivery to Kiesselbach's area. Active dose in the rat is 1 mg/kg body weight administered intravenously. One method of treating vasomotor symptoms may be to topically administer DIPA-1-8 or 2-6, or 2-7 via the intranasal route. The systemic effects of the DAPA compound will then give rise to cooling sensations to counteract activation of central heat-loss mechanisms (vasodilatation and sweating). In Case Study 4, this phenomenon was observed. The intranasal route of administration can also be used for the treatment of heat stress.

An adjunct used in pharmaceuticals or cosmeceuticals is an additional substance, treatment, or procedure used for increasing the efficacy or safety of the primary substance, treatment, or procedure or for facilitating its performance. The DAPA compounds relieve sensory discomfort in the nasal cavity. It is possible that they be used as adjuncts with other pharmaceuticals for this site.

An adjunct such as DIPA-1-8 will facilitate "apparent" efficacy of another primary ingredient, and thereby improve patient satisfaction and adherence to a dosage schedule. For example, DIPA-1-8 may be combined with an intranasal anti-inflammatory steroid. The preparation may be more desirable than the anti-inflammatory steroid alone, which takes longer to act. Anti-inflammatory steroids used for intranasal applications include such fluticasone propionate and mometasone furoate and older agents such as budesonide, flunisolide, beclomethasone diproprionate and triamcinolone acetonide. Other examples of intranasal drugs which may be combined with the DAPA compounds of this discovery include: antihistamines for intranasal applications such as olopatadine, azeleastine, and levocabastine; sympathomimetic amine vasoconstrictors such as phenylephrine hydrochloride, oxymetazoline, naphazoline, and other imidazoline receptor agonists and ketorolac which is approved for nasal administration. The adjunct DIPA compound can be used for medications that are useful for human therapy as well as for veterinarian uses.

Study 4
Results of TRPM8, TRPA1, and TRPV1 Receptor Assays:

The in vitro effects of test compounds were evaluated on cloned hTRPM8 channel (encoded by the human TRPM8 gene, expressed in CHO cells) using a Fluo-8 calcium kit and a Fluorescence Imaging Plate Reader (FLIP-RTETRA™) instrument. To examine the specificity of the test compounds, further tests were conducted on TRPV1 channels (human TRPV1 gene expressed in HEK293 cells) and TRPA1 channels (human TRPA1 gene expressed in CHO cells). The assays were conducted by ChanTest Corporation, 14656 Neo Parkway, Cleveland, Ohio 44128, USA.

Test compounds and positive control solutions were prepared by diluting stock solutions in a HEPES-buffered physiological saline (HBPS) solution. The test compound and control formulations were loaded in polypropylene or glass-lined 384-well plates, and placed into the FLIPR instrument (Molecular Devices Corporation, Union City, Calif., USA). The test compounds were evaluated at 4 or 8 concentrations with n=4 replicates per determination. The positive control reference compound was L-menthol, a known TRPM8 agonist. The test cells were Chinese Hamster Ovary (CHO) cells stably transfected with human TRPM8 cDNAs.

For FLIPRTETRA™ assay, cells were plated in 384-well black wall, flat clear-bottom microtiter plates (Type: BD Biocoat Poly-D-Lysine Multiwell Cell Culture Plate) at approximately 30,000 cells per well. Cells were incubated at 37° C. overnight to reach a near confluent monolayer appropriate for use in a fluorescence assay. The test procedure was to remove the growth media and to add 40 μL of HBPS containing Fluo-8 for 30 minutes at 37° C. 10 μL of test compound, vehicle, or control solutions in HBPS were added to each well and read for 4 minutes.

Concentration-response data were analyzed via the FLIPR Control software that is supplied with the FLIPR System (MDS-AT) and fitted to a Hill equation of the following form:

$$\text{RESPONSE} = \text{Base} + \frac{\text{Max} - \text{Base}}{1 + \left(\frac{xhalf}{x}\right)^{rate}}$$

where: "Base" is the response at low concentrations of test compound; "Max" is the maximum response at high concentrations; "xhalf" is the $EC_{50}$, the concentration of test compound producing half-maximal activation; and "rate" is the Hill coefficient. Nonlinear least squares fits were made assuming a simple one-to-one binding model. The 95% Confidence Interval was obtained using the GraphPad Prism 6 software.

Of the 12 compounds tested, all showed full efficacy on the TRPM8 receptor, i.e., at higher tested concentrations there was ~100% stimulation of calcium entry, and the data fitted a sigmoidal dose-response curve. The results for 10 of the compounds of this invention are illustrated in FIG. 4.

Figure 4:
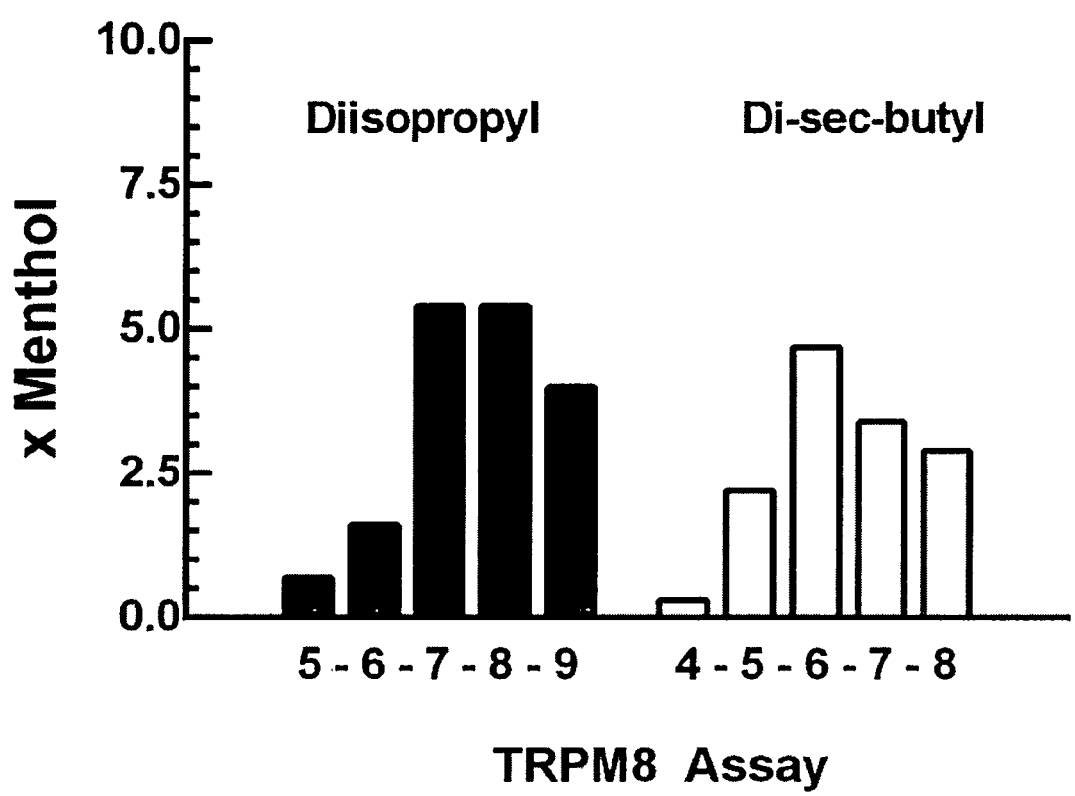
FIG. 4. is a graph of TRPM8 potency of Diisopropyl-phosphinoyl-alkane and Di-sec-butyl-phosphinoyl alkane analogs in the in vitro TRPM8 assay. Units are in comparison to l-menthol potency in the same assay. The numbers on the abscissa represent the number of carbons in one of the n-alkyl side-chain: that is, the 4-5-6-7-8-9 represents the butyl, pentyl, hexyl, heptyl, octyl, and nonyl group, respectively.

FIG. 4 is a graph of TRPM8 potency of Diisopropylphosphinoyl and Di-sec-butyl phosphinoyl alkane analogs in the in vitro TRPM8 assay. Units are in comparison to l-menthol potency in the same assay. The numbers on the abscissa represent the number of carbons in one of the n-alkyl side-chain: namely, the 4-5-6-7-8-9 represents the butyl, pentyl, hexyl, heptyl, octyl, and nonyl group, respectively.

The $EC_{50}$ of the more potent compounds (DIPA-1-7, DIPA-1-8, DIPA-1-9, 2-5, 2-6, 2-7, 2-8) fell within a narrow range with overlapping 95% Confidence Intervals. [Table 3] The potency of DIPA-1-7 and DIPA-1-8 are similar and significantly greater than the potencies of DIPA-1-5 and DIPA-1-6. By contrast the structural modifications of comparative compounds 3-1 and 3-2 resulted in a significant loss of bioactivity. DIPA-1-10 was synthesized at a later time and tested by David Andersson of King's College, London, U.K. It was found to be 2.4× less active than DIPA-1-9 [or 1.7× menthol on Table 3]. The data for DIPA-1-10 is not included in the Table 3 or Figure because it was obtained under different assay conditions.

To examine the specificity of the test compounds, further studies were conducted on TRPV1 channels (human TRPV1 gene expressed in HEK293 cells) and TRPA1 channels (human TRPA1 gene expressed in CHO cells). The test cells were Chinese Hamster Ovary (CHO) cells or Human Embyronic Kidney (HEK) 293 cells transfected with human TRPV1 or TRPA1 cDNAs. The positive control reference compound was capsaicin (a known TRPV1 agonist) or mustard oil (a known TRPA1 agonist). DIPA-1-7 and DIPA-1-8 did not exhibit any agonist on antagonist activity on TRPA1 channels at maximum tested concentrations of 100 μM. The results for DIPA-1-8 are shown in FIG. 5.

Figure 5:
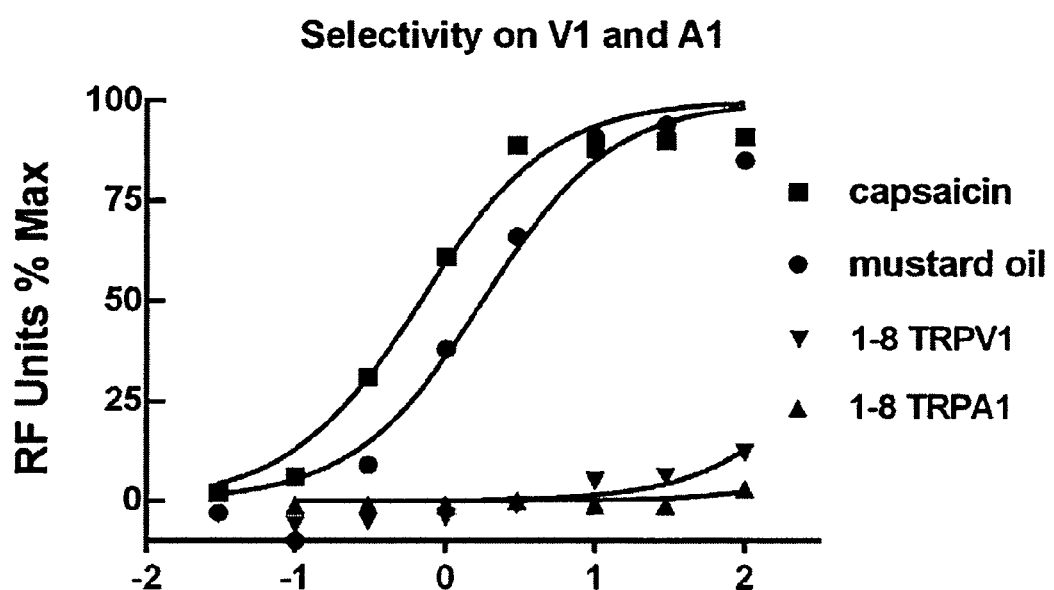
FIG. 5. is a graph showing the lack of agonist activity of DIPA-1-8 in cells transfected with TRPV1 or TRPA1 plasmids. The positive controls capsaicin and mustard oil for TRPV1 and TRPA1 are active, respectively, but DIPA-1-8 is not active in these TRPV1 or TRPA1 transfected cells. The ordinate is given in Relative Fluorescence Units % of maximum, which measure calcium entry into the transfected cells and the abscissa is the logarithm of the concentration of the test compound.

FIG. 5 shows the lack of agonist activity of DIPA-1-8 in cells transfected with TRPV1 or TRPA1 plasmids. The positive controls capsaicin and mustard oil for TRPV1 and TRPA1 are active, but DIPA-1-8 is not. The ordinate is given in Relative Fluorescence Units; % of maximum, which measure calcium entry into the transfected cells and the abscissa is the logarithm of the concentration of the test compound. DIPA-1-8 was also devoid of antagonist activity against TRPV1 or TRPA1.

The $EC_{50}$ values do not give information on the quality of the heat abstraction sensation in the nasal cavity, on the duration of action, or on the accessibility [distribution] of the molecule to tissue targets such as the nasal mucosa. The $EC_{50}$ however, gives guidance on the relative potencies of the different analogs. Of special importance is the differentiation of the drug effect on the keratinized epithelia of the nose [nostril skin and vestibule] versus the non-keratinizing epithelia of the nasal mucosa. The use of the aqueous solution on the swab makes the drug available to all epithelia. The identification of agents that are optimized for the nasal mucosa requires bioassays that directly address these questions. Part of the discovery process here is the recognition that stimulation of cold receptors on the keratinized surfaces is not desirable, whereas stimulation of the mucosal receptors on Kiesselbach's area gives the desired drug effect. Both responses are likely to be mediated by the TRPM8 receptor protein and correlated to the $EC_{50}$. The presence of 15 to 16 carbons in molecules of Formula 1 appear to optimize the localization and distribution of the drug candidate to the nasal mucosa.

TABLE 3

$EC_{50}$ and relative potency of compounds on TRPM8..

| Code | $EC_{50}$ µM | 95% Confidence Interval | Relative Potency |
| --- | --- | --- | --- |
| Menthol | 3.8 | 2.5 to 5.6 | 1.0 |
| DIPA-1-5 | 5.6 | 4.4 to 7.2 | 0.7 |
| DIPA-1-6 | 2.4 | 1.5 to 4.0 | 1.6 |
| DIPA-1-7 | 0.7 | 0.5 to 1.0 | 5.4 |
| DIPA-1-8 | 0.7 | 0.5 to 1.0 | 5.4 |
| DIPA-1-9 | 0.9 | 0.4 to 2.5 | 4.0 |
| 2-4 | 14.5 | 7 to 29 | 0.3 |
| 2-5 | 1.7 | 1.0 to 2.9 | 2.2 |
| 2-6 | 0.8 | 0.5 to 1.3 | 4.7 |
| 2-7 | 1.1 | 0.6 to 2.3 | 3.4 |
| 2-8 | 1.3 | 0.7 to 2.3 | 2.9 |
| 3-1 | 24 | 8 to 76 | 0.2 |
| 3-2 | 4.2 | 1.6 to 10.8 | 0.9 |

Study 5
Activity in Laboratory Rat: Perioral, Topical and Intravenous Delivery

To get a better idea on the in vivo activity of these DAPA compounds further studies were conducted on the laboratory rat after administration of the test compounds by three different routes: intravenous, perioral, and topical. Variation on the routes of administration provides information on the ability of the molecule to cross membrane barriers.

Fur-coated and feathered animals—when wet and cold—shake, like a wet dog (see, e.g., Dickerson et al., 2012; Ortega-Jimenez et al., 2012; Wei, 1981). These shakes are rapid alternating contractions of the supination and pronation muscles about the spinal axis, and can be readily observed and counted. "Wet-dog shaking" has been studied in detail in animals and this behaviour is interpreted to have survival value because shaking, by removing the water off t skin, reduces the need to expend evaporative energy to remove wetness. The triggering sensation for shaking is thus having water trapped in between hair follicles or feathers. Humans have little hair on skin and do not shake. The likely equivalent behaviour to shaking in humans is shivering, a condition caused by generalized sensations of coolness/cold and wetness.

Drug-induced shaking in animals has been reviewed (see, e.g., Wei, 1981). Under the right conditions, drug-induced shaking can be observed in the pentobarbital-anesthetized rat, enhanced by hypothermia and cold, and inhibited by elevating body temperature.

In experiments conducted here, test compounds were evaluated for "wet-dog shaking" as a model of cooling sensation. Using a standardized procedure, test compounds were compared in their ability to stimulate the shaking response by perioral administration, by topical delivery to the abdominal skin, and by intravenous administration through a cannulated femoral vein.

Perioral. Test compounds were dissolved in saline and administered by oral gavage to pentobarbital-anesthetized male albino rats at 20 mg/kg at a volume of 0.1 mL/100 g body weight [N=3 to 4 rats per compound]. Shaking was counted over a 40 min period and recorded at 10-min intervals. The results are shown in FIG. 6.

FIG. 6 shows shaking frequency of pentobarbital-anesthetized male rats after perioral administration of test compounds at 20 mg/kg with a gavage needle. Shaking frequency was counted for 40 min. The surprising lack of activity in the di-sec-butyl-analogs is noted.

Three of the four "diisopropyl" compounds caused vigorous shaking. The "di-sec-butyl" compounds were relatively inactive, except 2-5 which elicited an average of 4 shakes in the 40 min observation period. By contrast, DIPA-1-5, DIPA-1-6, and DIPA-1-7 produced an average shaking frequency of 86, 56, and 36 shakes, respectively. The strong activity of DIPA-1-5 was unusual. Applied to the skin, DIPA-1-5 has a refreshing cooling sensation, but the duration of action of only about 30 min was significantly less than that for DIPA-1-6 and DIPA-1-7. It is possible that its smaller molecular size facilitates absorption and allows greater access to systemic receptors, and therefore more shaking.

The relationship of the shake response to temperature sensation was further studied [in pentobarbital-anesthetized rats]. After injection of the sodium pentobarbital anesthetic, rectal temperature drops, and reaches approximately 35° C. in about 10 min. This hypothermia can be reversed by placing the animal on a heated surface and body temperature maintained at 38° C. DIPA-1-7 20 mg/kg perioral elicited 36±5 shakes (N=6) in the anesthetized rat, but in the heated animals, the shaking frequency was significantly reduced to 5±2 shakes (N=6) [P<0.001]. The reduction of shaking frequency by ⅔ under heat indicated that the shake response was linked to cold sensations and shivering.

Topical. Shaking is an excellent indicator of in vivo effect. Methods were developed to determine if shaking was seen after topical application of DAPA compounds. The abdominal skin of the pentobarbital-anesthetized rat was shaved and 20 µL of the pure unadulterated DIPA chemical was applied with a micropipette on a ~1 cm diameter circle of skin, enclosed with a ring of cream [Baby cream "Nevskaya kosmetika Detskyi" Nevskaya Kosmetika Inc., Saint-Petersburg 192029], as shown in FIG. 7. The number of shakes was counted for 1 hr after application.

FIG. 7 shows shaking frequency of pentobarbital-anesthetized male rats after 20 µL of the pure test compounds was delivered onto the abdominal skin. Test substances were applied with a micropipette to the center of a circle enclosed by cream on the shaved skin, as shown in the cartoon insert on the graph. Shaking frequency was counted for 1 hr. The surprising lack of activity in the di-sec-butyl-analogs after transdermal delivery is noted.

The results for topical, perioral, and intravenous responses are summarized in Table 5. The surprising potency of DIPA-1-5 and DIPA-1-6 was unexpected but similar to what was seen with perioral administration. These smaller may penetrate faster through the skin barrier and go into the systemic circulation. However, the value of this fast action is uncertain. In most contemplated topical applications of this discovery, the preference is for the drug action to remain localized and not systemic.

Intravenous. When the relative activities of the analogs for producing shaking by the perioral and topical routes were compared to the $EC_{50}$ for TRPM8 activation [as inversely measured by the xMenthol potency] it can be seen that the two variables are not correlated. For example, 2-6 is 4.7× menthol, but does not produce shaking by perioral or topical administration. Yet DIPA1-7, which 5.7× menthol, produces vigorous shaking by these routes. The lack of quantitative correlation is perplexing, because it would be expected that the cooling properties are linked to TRPM8 activation. To clarify the discrepancy, the test compounds were compared by the intravenous [i.v.] route of administration, a delivery route which is less influenced by membrane barriers.

Male rats weighing ~220-240 g were anesthetized with sodium pentobarbital, 55 mg/kg intraperitoneal, and after the loss of the righting reflex, animals were placed on a heated table and body temperature maintained at 37 to 38° C. The femoral vein was cannulated with PE-20 tubing connected to a 1 mL syringe. Stock solutions were prepared in normal saline at 10 mg/mL and further diluted to 2 mg/mL on the day of the experiment and injected at 0.1 mL/100 g body weight to give a dose of 1 mg/kg i.v. There were N=3 to 6 per test substance. Shaking frequency was counted for 30 min after i.v. delivery and the results compared with the Student's t-test. Two trials were conducted per animal with a 10 to 15 min interval between doses. The shaking frequency after intravenous injections is shown in FIG. 8.

Figure 8:
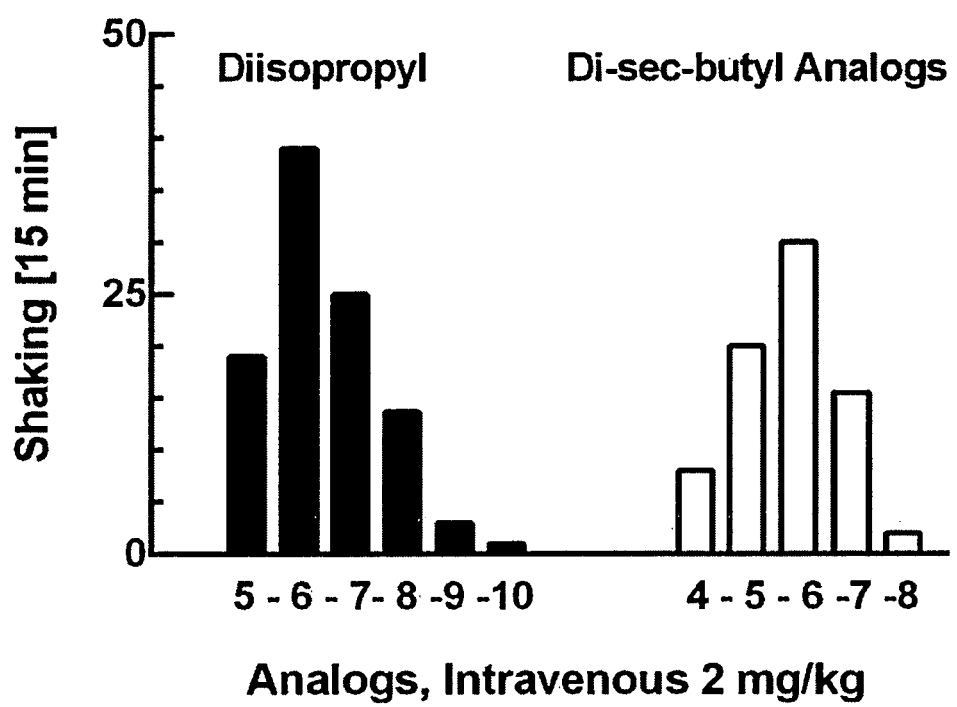
FIG. 8. is a graph showing shaking frequency of pentobarbital-anesthetized male rats after intravenous injection of 2 mg/kg of test compounds. Each rat was given two injections with a 30 min interval. The graph shows the $2^{nd}$ trial data. Shaking frequency was counted for 15 min after injection. The numbers on the abscissa represent the number of carbons in one of the n-alkyl side-chain: that is, the 4-5-6-7-8-9-10 represents the butyl, pentyl, hexyl, heptyl, octyl, nonyl and decanyl group, respectively.

FIG. 8 shows shaking frequency of pentobarbital-anesthetized male rats after intravenous [i.v.] injection of 2 mg/kg of test compounds. Each rat was given two injections with a 30 min interval. The graph shows the $2^{nd}$ trial data. Shaking frequency was counted for 15 min after injection.

Shaking was observed immediately after i.v. injection and at least 78% of the total shakes occurred in the first 5 min after injection. The response in the second trial was at least as robust in the first trial, showing the lack of desensitization [FIG. 9]. The greater response in the second trial may be due to cumulative effects or a lightening of anesthesia.

Figure 9:
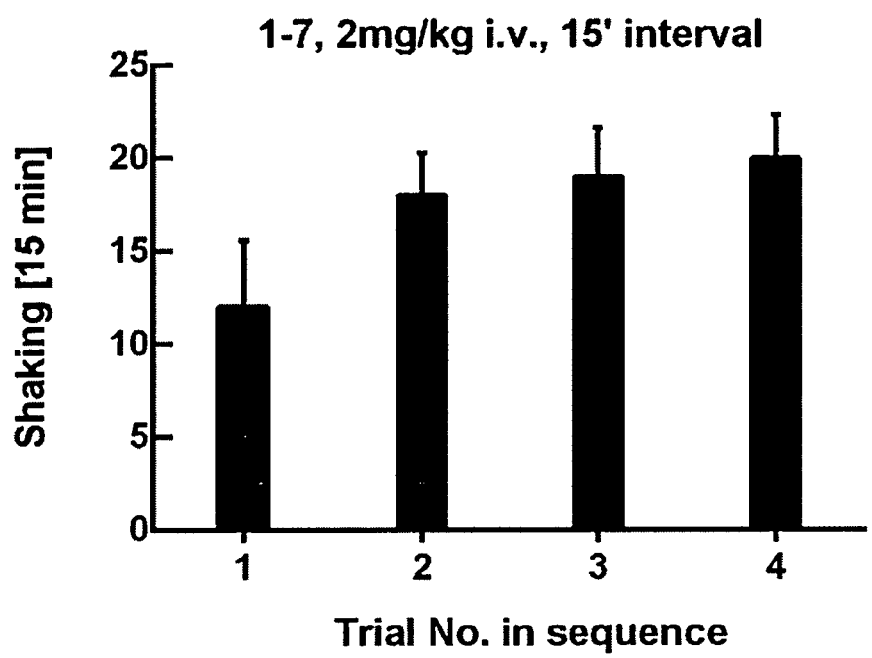
FIG. 9. is a graph showing the absence of tachyphylaxis to the shaking effects of repeated injections of DIPA-1-7, 2 mg/kg intravenous, at 15 min intervals. It can be seen that the shaking intensity of the $3^{rd}$ and $4^{th}$ trials were not diminished by the previous injections.

FIG. 9 shows the absence of tachyphylaxis [desensitization] to the shaking effects of repeated injections of DIPA-1-7, 2 mg/kg intravenous, at 15 min intervals. It can be seen that the shaking intensity of the $3^{rd}$ and $4^{th}$ trials were not diminished by the previous injections.

TABLE 4

Shaking frequency after perioral [per 20 mg/kg body weight] or topical delivery of 20 µl test compounds [per animal] to the anesthetized rat.

| Code | Mol Wt | # Cs | xMenthol | Perioral | Topical | Intravenous |
|---|---|---|---|---|---|---|
| DIPA-1-5 | 204 | 11 | 0.7 | 86 ± 7 | 138 ± 15 | 19 ± 3 |
| DIPA-1-6 | 218 | 12 | 1.6 | 56 ± 5 | 69 ± 8 | 39 ± 4 |
| DIPA-1-7 | 232 | 13 | 5.4 | 36 ± 4 | 79 ± 8 | 25 ± 3 |
| DIPA-1-8 | 246 | 14 | 5.4 | 0 | 7 ± 2 | 14 ± 2 |
| DIPA-1-9 | 260 | 15 | 4.0 | 0 | 0 | 3 ± 1 |
| 2-4 | 218 | 12 | 0.3 | 0 | 0 | 8 ± 2 |
| 2-5 | 232 | 13 | 2.2 | 4 ± 1 | 0 | 20 ± 2 |
| 2-6 | 246 | 14 | 4.7 | 0 | 0 | 30 ± 3 |
| 2-7 | 260 | 15 | 3.4 | 0 | 0 | 15 ± 2 |
| 2-8 | 274 | 16 | 2.9 | 0 | 0 | 2. |

Interpretation of $EC_{50}$ and Shaking Data after Perioral, Topical and Intravenous Delivery The strong bioactivity of intravenous 2-6 and 2-7 is in sharp contrast to the results seen after perioral or topical delivery when no shaking was observed. These results provide strong objective laboratory evidence that the DIPA compounds of Table 2A are qualitatively different from the corresponding di-sec-butyl compounds. The diisopropyl compounds produce shaking by all three routes of administration, whereas the di-sec-butyl compound is active only by intravenous delivery.

The TRPM8 $EC_{50}$ and perioral, topical, and intravenous provides an excellent framework and rationale for the selection of the best API for nasal discomfort.

The less potent candidates on the TRPM8 $EC_{50}$, namely, 1-5, 1-6, 2-4 and 1-10 were judged to be less suitable because of a lack of activation power.

The perioral and topical shaking seen with 1-5, 1-6 and DIPA-1-7 made these candidates less attractive because shaking is elicited by strong sensory stimuli, and this is not desirable in the nasal cavity. The extra penetrating quality of DIPA-1-7 may, however, be useful in congested situations such as the common cold and severe sinusitis.

The lack of activity of DIPA-1-8, DIPA-1-9, 2-6 and 2-7 on perioral and topical administration made these analogs attractive because it meant that these molecules remained localized in tissues after administration.

The greater shaking frequency see with 2-6 and 2-7 versus DIPA-1-8 and DIPA-1-9 meant that these molecules produced stronger sensations of cold, an effect which was confirmed on nostril skin.

From this analysis of the four measurements, namely, TRPM8 $EC_{50}$ and perioral, topical, and intravenous shaking activity, the logical initial choices for nasal discomfort is DIPA-1-8 and DIPA-1-9, followed by 2-6 and 2-7. DIPA-1-9 is especially attractive because it does not cause shaking, and yet is potent on the TRPM8 receptor.

Study 6

Screening of Compounds and Case Studies in Human Subjects

In these studies, subjects were given dosages units containing 1.5 to 1.75 mL of DAPA compounds stored in 2.0 mL microcentrifuge tubes (Nova Biostorage Plus, Canonsburg, Pa. 15317) and cotton swab (Puritan large cotton tipped applicators, Model 803-PCL) or SwabDose units, made by Unicep Corp., containing 2 mg/mL of DIPA-1-9. The tested compounds were as a solution in distilled water or in 1 mL of purified USP water. The range of tested concentrations was 1 to 4 mg/mL. The subjects were given instructions on how to place the tip of the applicator in the nostril, to gently compress the nostril with the thumb and forefinger to distribute the liquid into the Kiesselbach area. Approximately 0.03 mL to 0.06 mL is delivered by this method of application to the nasal cavity. A larger volume was occasionally delivered if the subject excessively wetted the cotton tipped applicator.

For a 2 mg/mL DAPA compound the estimated delivered dose to both nostrils of the nose is 2 mg/mL×0.045 mL, or approximately 90 µg. This is comparable to the potency of intranasal steroids used for allergic rhinitis: for example, 55 µg of triamcinolone acetonide is delivered per actuation of a spray bottle of Nasacort®.

Three subjects, two with defined seasonal allergic rhinitis and one subject with chronic rhinitis of unknown cause, volunteered to be subjects for testing for multiple sessions. The compounds in Table 5 were tested when the subjects were symptomatic: i.e. were sneezing or had rhinorrhea, or had itchy sensations in the nose and eyes. The subjects refrained from the use of any antihistamine or intranasal steroids during the test periods, which lasted for six weeks. Subjects were instructed to rinse the nose with water if there was any nasal discomfort: however, irritation and discomfort was not seen in these trials.

These observations were made. The DIPA compounds 1-8 and 1-9 (1-[Diisopropyl-phosphinoyl]-octane and 1-[Diisopropyl-phosphinoyl]-nonane]), respectively, rapidly inhibit sneezing and rhinorrhea, within 5 to 10 min after application, and these effects were long-lasting: for 12 hr or more after a single instillation. The subjective feeling of nasal cavity discomfort was removed and breathing felt clear and normal. DIPA-1-9 had a slight refreshing sensation on the nasal mucosa after application, whereas DIPA-1-8 produced a sense of coolness lasting for approximately 15 min. The strong, efficacious drug action is unusual and has not been previously recognized to be achievable, and was surprising and amazing.

The two 1-[Di-sec-butyl-phosphinoyl]-alkanes of equal molecular weight and total number of carbons [14 and 15] to DIPA-1-8 and DIPA-1-9, namely, 2-6 and 2-7 1-[Di-sec-butyl-phosphinoyl]-hexane and 1-[Di-sec-butyl-phosphinoyl]-heptane], respectively, also exhibited efficacy. 2-6 and 2-7 had a stronger cooling action on the nasal mucosa and on the nostril skin after application. At higher doses, 2-6 and 2-7 sometimes triggered sneezing and long-lasting cooling on the skin on the tip of the nose. These side-effects may limit their use. But if nasal discomfort is not controlled by DIPA-1-8 or DIPA-1-9, then 2-6 and 2-7 are good back-up compounds.

For the other compounds, with total carbons numbers different from 14 or 15, good control of the symptoms of rhinitis was not achieved. For the two analogs with 13 carbons, DIPA-1-7 and 2-5, robust sensations were felt on the nostril skin and the nasal mucosa, but the beneficial effects on rhinitis were not evident. Both molecules seemed to induce rhinorrhea in some trials, perhaps reflecting a strong sensory action on cold receptors or on serous glands. For the two analogs with 16 carbons, 1-10 and 2-8, cooling sensations were minimally present after instillation, but there was little evidence of reducing the symptoms of rhinitis. In one subject 2-8 appeared to increase "stuffiness" at the higher concentration of 4 mg/mL.

These results of the various analogs are consistent with the TRPM8 $EC_{50}$ data, and the shaking data seen after intravenous, perioral and topical administration. The diminished activities of 1-10 and 2-8 are consistent with a lack of potency on TRPM8. DIPA-1-7 is very active on cold sensations and TRPM8, but its ability to penetrate and distribute in tissues is reflected in its shaking activity after perioral and topical administration. This is undesirable because the molecule will move away from its intended target site. DIPA-1-7 and 2-5 are both smaller molecules, having 13 carbons, and have greater mobility in tissues. Thus, DIPA-1-7 and 2-5 act on keratinized skin and do not localize at Kiesselbach's area, and this limits efficacy.

The four compounds with 14 or 15 carbons, namely DIPA-1-8, DIPA-1-9, 2-6, and 2-7, are potent on TRPM8 and do not produce shaking after perioral or topical administration. This means that the drug is potent and also remains localized at its site of application: a highly desirable characteristic. Shaking may represent the ability of the molecule to produce a sensation of "stinging cold", and the diminished activity of DIPA-1-9 on this end-point makes it the lead candidate. DIPA-1-8 is the second lead candidate, followed by 2-6 and 2-7. The more intense cold seen with 2-6 suggests that it may be a preferred candidate for modifications of conditions such as sinusitis, heat stress, and "night sweats". In these conditions, a stronger sense of cold may have better therapeutic value.

In summary, the pattern of activity of each molecule is a sum of penetration, distribution, localization, and intrinsic activity at the receptor. The best compounds are those that have potency on the nasal mucosa, and not on the keratinized skin of the nares and nasal vestibule The best compounds of the present discovery for nasal discomfort are DIPA-1-8 and DIPA-1-9, and 2-6 and 2-7, and are examples of 1-[Dialkyl-phosphinoyl]-alkanes $[(O=)PR_1R_2R_3]$ wherein each of $R_1$, $R_2$, is either isopropyl or sec-butyl and $R_3$ is a linear alkyl group of 6 to 9 carbons, and wherein the preferred embodiments have 15 or 16 carbons.

Case studies are described below which illustrate the use of several DAPA compounds delivered to Kiesselbach's area with a swab. The preferred embodiments are effective:
  to reduce the discomfort of allergic rhinitis;
  to reduce the discomfort of vasomotor rhinitis;
  to reduce sneezing and rhinorrhea;
  to enhance the sense of breathing fresh air in normal subjects;
  to reduce the discomfort of breathing polluted air;
  to enhance breathing comfort and performance in a professional athlete;
  to help an individual cope with heat stress; and
  to reduce the severity of "night sweats" in a subject.

TABLE 5

Test Results of Compounds on Nasal Discomfort Caused by Rhinitis

| Chemical Code | No. Carbons | Mol. Wt. | Efficacy | Side-effects |
| --- | --- | --- | --- | --- |
| DIPA-1-7, 2-5 | 13 | 232.34 | + | cold, rhinorrhea |
| DIPA-1-8, 2-6 | 14 | 246.37 | +++ | cold skin for 2-6 |
| DIPA-1-9, 2-7 | 15 | 260.40 | +++ | cold skin for 2-7 |
| DIPA-1-10, 2-8 | 16 | 274.44 | 0 | congestion |

Case Study 1

A 70-year old male subject had long-standing seasonal allergic rhinitis since he first noticed nasal symptoms on a golf course in spring, 45 years ago. The likely trigger was grass pollen because the allergy manifested itself most often after rainstorms followed by periods of dry weather. Over the years, he learned to control nasal congestion and rhinorrhea with oral antihistamines by taking a daily dose of 10 mg of loratadine, supplemented during the hay fever season by two 60 mg fexofenadine tablets daily, and when necessary 5 mg of chlorpheniramine. He had tried an intranasal steroid spray [Flonase®], but found the delivery method "messy" and leaving objectionable sensations in the nose and mouth which interfered with gustation.

This season his allergy was heralded by the onset of severe bouts of violent sneezing, about 10 to 15 sneezes in a 15 min period, followed by rhinorrhea and congestion. He volunteered to try the DAPA compounds of this discovery and stopped using oral antihistamines. He started with a DIPA-1-9 2 mg/mL swab and right away noticed the disappearance of sneezing and rhinorrhea which lasted for at least 12 hr. He found that a single daily DIPA-1-9 1 mL swab was sufficient to block all symptoms of hay fever. No odor, irritation, or taste was detected from the swab. The individual had a sense of free and unobstructed airflow in the nasal cavity. He no longer used any oral antihistamines.

This individual then volunteered to repeat the experience with other analogs with some of the results as shown in Table 5. He noted the cooling effects of 2-6 and 2-7 on the nostril skin, and some initial itching and rhinorrhea with these compounds. But he was also sure that these analogs were effective in preventing the symptoms of hay fever. He tried swabs with DIPA-1-8 at a higher concentration of 4 mg/mL and waited for hay fever symptoms to recur. To his surprise, symptoms did not recur until after 5 days. He said it was as if the drug had cured the disease. His wife also noted that he had stopped snoring and snorting during sleep when he was using the swabs. Swabbing with just distilled water was not effective in controlling his hay fever symptoms. He pronounced his cure as being "miraculous" because the rhinorrhea disappeared, although he still had an occasional sneeze. The only side effect he noted from the DAPA compounds was occasional stuffiness because of crusted and dried mucus on his nasal membranes. This problem was easily solved by rinsing his nose with tap water.

Case Study 2

A 50-year old male subject is a distinguished scientist at a world-renowned institute of research in physiology. He has a MD and a PhD degree. The subject suffers from perennial rhinitis of many years. He stated that the rhinorrhea is "always there" and seeing specialists and taking standard medications such as intranasal steroids and antihistamines were minimally effective to help control the symptoms. He noted that on average his rhinorrhea can be estimated by the 10 Kleenex tissues he deposits each day into his waste paper basket! He volunteered to try swabs containing DIPA-1-9, 2 mg/mL and was given instructions on how to apply the solution onto Kiesselbach's area. He reports that "The results are truly amazing. For the first time in many years, I woke up in the morning without any rhinorrhea." He noted that he now uses zero or only one or two Kleenex tissues for his nose each day. He remarked on the "strong drying effect on the mucous membranes of the nasal cavity after repeated use" and suggested that there might be an inhibitory drug effect on serous gland secretion in the nasal mucosa. When asked if he felt coolness or cold when applying DIPA-1-9 2 mg/mL into his nostril, he said "neither term is correct; the sensation is of comfortable freshness." He was of the opinion that a slightly higher concentration, e.g. 3 or 4 mg/mL of DIPA-1-8 or DIPA-1-9 instead of 2 mg/mL might be more effective in gaining full control of his rhinorrhea.

A 65-year old male is retired and lives in Las Vegas, in a gated community with a golf course. But during spring he suffers severely from allergic rhinitis and allergic conjunctivitis. The conjunctivitis is especially annoying because he likes to play in professional poker tournaments. He volunteered to try the DIPA-1-9 2 mg/mL swabs and noted that it worked well for his rhinitis. Surprisingly, he also found that his pruritic conjunctivitis was relieved. Upon closer questioning, it was clear that he did not apply the swabs to his eyes but had used generous amounts in his nasal cavity. He had been instructed to squeeze his nostrils gently to disperse the liquid over Kiesselbach's area. Apparently, he had applied too much liquid and squeezed the applied droplets so that there was retrograde flow up the nasal-lachrymal duct so that his eyelids received the DIPA-1-9 formulation. He remarked that his eyelids felt cool and comfortable and the itchiness in his eyes was gone.

Case Study 3

A 45-year old female subject was a professional tennis player. She had nasal congestion from the common cold before an important match and asked if she could try the swab. She was given a swab containing 4 mg/mL of 2-6. She said the swab was fully effective in reducing her congestion and she was very pleased that she won her match. Subsequently, she went to Hong Kong to visit her grandfather. It was in February and she noted the air pollution was severe, and going out into the streets gave her the sniffles. She had been given swabs containing DIPA-1-9 2 mg/mL and she said use of these swabs reduced the irritant effects of breathing the polluted air.

The efficacy of the swabs in controlling the symptoms of nasal stuffiness from the common cold was confirmed in two other subjects. The effects, however, were not as dramatic as with hay fever symptoms. One subject remarked that when "The nose was completely stuffed up, it was difficult to inhale and self-administer the contents of the swab." It is more likely that the common cold virus causes a wider area of inflammation on the turbinate mucosa, and hence localized drug in Kiesselbach's area is less able to abrogate the sense of stuffiness. Nevertheless, there was a beneficial effect on the subjective symptoms of congestion from the common cold.

Case Study 4

A 71-year old woman had occasional bouts of hot flushes/night sweats. She was on hormone replacement therapy (HRT) (estradiol 1 mg and medroxyprogesterone 2.5 g, once per day), but decided to stop HRT after her physician warned her about the risks of breast cancer and uterine cancer. Her episodes of night sweats became more frequent and this was frustrating to her because it was necessary to change the bed sheets frequently. She agreed to try a swab containing 4 mg/mL 2-6. The swab was applied to the Kiesselbach's area before going to sleep at night. She remarked that the swab made her nasal passages feel cool and it sent "shivers down her spine", especially if it the weather was rainy and cold. No episodes of night sweats were observed for the three days when she used the swabs, and in the following four weeks of observation. The results are promising but a larger sample is required to determine if there is a significant drug effect in the control of "night sweats". She remarked that the swabs are likely to be value for treating heat discomfort when travelling to hot countries such as Egypt and Thailand.

Case Study 5

A 45-year old male subject with severe seasonal rhinitis volunteered to test various substances by intranasal swab delivery. He had previously tried the Zicam Nasal Swabs for "gentle Allergy Relief" but noted that the gel on the swabs felt a little bit "slippery" and uncomfortable when applied to the nasal cavity. He said that the instructions and information on the Zicam box was "use 1 tube every 4 hours" and "optimal results may not be seen for 1 to 2 weeks." He said that the gel congealed after opening in less than 24 hr so it was not possible to use the same swab for multiple applications.

He tried the DIPA-1-9 2 mg/mL swab with and without the addition of CPS-030 5 mg/mL. He noted that the CPS-030 added swab had a faster onset of cooling action, but may have also increased his rhinorrhea. Monomenthyl glutarate and Cooler 10 added to DIPA-1-9 at 8 mg/mL did not enhance efficacy when tested in this subject. The DIPA-1-9 swab, however, effectively controlled his symptoms, especially the sneezing, with an immediate onset of effect.

He only had to use the same swab and apply it twice a day to gain complete control of his symptoms. This subject remarked that icilin powder, inhaled from the radial fossa, was still the best medication for him because one dose was sufficient for 24 hr control of his symptoms. He recommended that the icilin powder be added to the DIPA-1-9 swab. Overall, he was very pleased with the efficacy of the DIPA-1-9 swab.

In summary, a new class of compounds has been identified to treat the nasal discomforts associated with rhinitis and nasal irritants. These molecules are preferably applied with a swab, in an aqueous solution of the active ingredient, to Kiesselbach's area.

REFERENCES

A number of publications are cited herein in order to more fully describe and disclose the discovery and the state of the art to which the discovery pertains. Each of these publications is incorporated herein by reference in its entirety into the present disclosure.

The invention claimed is:

1. A method of relieving sensory discomfort in a nasal cavity, comprising:

providing an aqueous liquid composition, the composition having a therapeutic amount of 1-[Diisopropyl-phosphinoyl]-nonane; and, topically applying the aqueous liquid composition to the Kiesselbach's area of a human nose in need thereof to relieve nasal discomfort caused by air pollutants, rhinitis, the common cold or rhinosinusitis.

2. The method of relieving sensory discomfort in the nasal cavity as in claim 1, wherein the therapeutic amount of 1-[Diisopropyl-phosphinoyl]-nonane is 1 to 10 mg/mL of the composition.

3. The method of relieving sensory discomfort in the nasal cavity as in claim 2 wherein the aqueous liquid composition is saturating an absorbent material.

* * * * *